US011864921B2

(12) United States Patent
Maderic et al.

(10) Patent No.: US 11,864,921 B2
(45) Date of Patent: Jan. 9, 2024

(54) MELANIN-BIAS REDUCING PULSE OXIMETER AND PATIENT MONITORING SYSTEMS AND DEVICES

(71) Applicant: JMad Creations, LLC, Bethlehem, PA (US)

(72) Inventors: Jonathan M. Maderic, Bethlehem, PA (US); Samantha Rose Elduff, Boston, MA (US); Jacob Martin Joyce, Gibsonia, PA (US)

(73) Assignee: JMAD CREATIONS, LLC, Bethlehem, PA (US)

( * ) Notice: Subject to any disclaimer, the term of this patent is extended or adjusted under 35 U.S.C. 154(b) by 0 days.

(21) Appl. No.: 17/883,068

(22) Filed: Aug. 8, 2022

(65) Prior Publication Data

US 2023/0043376 A1    Feb. 9, 2023

Related U.S. Application Data

(60) Provisional application No. 63/230,815, filed on Aug. 9, 2021.

(51) Int. Cl.
*A61B 5/0205* (2006.01)
*A61B 5/1455* (2006.01)
(Continued)

(52) U.S. Cl.
CPC ............ *A61B 5/7203* (2013.01); *A61B 5/002* (2013.01); *A61B 5/0205* (2013.01);
(Continued)

(58) Field of Classification Search
CPC . A61B 5/1455; A61B 5/14552; A61B 5/7203; A61B 5/002; A61B 5/0205;
(Continued)

(56) References Cited

U.S. PATENT DOCUMENTS 5,448,991 A    9/1995  Polson
5,792,052 A    8/1998  Isaacson
(Continued)

OTHER PUBLICATIONS

International Search Report and Written Opinion of PCT International Application No. PCT/US2022/039703, dated Dec. 6, 2022.
(Continued)

*Primary Examiner* — Eric F Winakur
(74) *Attorney, Agent, or Firm* — RAPHAEL BELLUM PLLC

(57) ABSTRACT

The melanin bias reducing pulse oximeter system reduces melanin interference when obtaining pulse oximetry readings for individuals with higher skin concentrations of melanin. The system incorporates optics reducing the melanin bias through hardware and software designed using extensive testing, via a proprietary testing method. The physical pulse oximeter includes different mechanical designs, for example, finger clip, ring, and bracelet design for enhanced usage, accuracy, and comfort for those unable to wear traditional pulse oximeters. The user interface includes built-in UI, external and portable UI, bedside monitoring, and connection to patient monitoring systems, via wired and/or wireless means. Further systems include those with both melanin bias reducing pulse oximetry and heart telemetry in the same device, via either a wired or wireless compact waterproof system to be used for continuous monitoring including blood oxygen saturation as a $5^{th}$ vital sign. Systems also include fall detection, bed alarm, and location services.

29 Claims, 29 Drawing Sheets

(51) Int. Cl.
*A61B 5/024* (2006.01)
*A61B 5/00* (2006.01)

(52) U.S. Cl.
CPC .......... *A61B 5/14552* (2013.01); *A61B 5/681* (2013.01); *A61B 5/7225* (2013.01); *A61B 5/742* (2013.01); *A61B 5/02433* (2013.01)

(58) Field of Classification Search
CPC ....... A61B 5/681; A61B 5/7225; A61B 5/742; A61B 5/02433
See application file for complete search history.

(56) References Cited

U.S. PATENT DOCUMENTS

| | | | | |
|---|---|---|---|---|
| 6,879,850 | B2* | 4/2005 | Kimball | A61B 5/14552 600/336 |
| 7,359,742 | B2 | 4/2008 | Maser | |
| 7,532,919 | B2* | 5/2009 | Soyemi | A61B 5/14551 600/323 |
| 7,570,979 | B2 | 8/2009 | Cooper | |
| 8,437,824 | B2* | 5/2013 | Moon | A61B 5/14552 600/323 |
| 9,179,868 | B2* | 11/2015 | Yu | A61B 5/14552 |
| 9,498,158 | B2 | 11/2016 | Isaacson | |
| 9,700,249 | B2 | 7/2017 | Johnson | |
| 10,674,961 | B2 | 6/2020 | Prior | |
| 10,820,863 | B2* | 11/2020 | Bechtel | A61B 5/14552 |
| 2006/0253007 | A1 | 11/2006 | Cheng | |
| 2014/0243612 | A1 | 8/2014 | Li | |
| 2016/0066827 | A1 | 3/2016 | Workman | |
| 2017/0265794 | A1 | 9/2017 | O'Donnell | |
| 2018/0256088 | A1 | 9/2018 | Ray | |
| 2019/0167124 | A1 | 6/2019 | Verkruijsse | |
| 2020/0015723 | A1 | 1/2020 | Eisen | |

OTHER PUBLICATIONS

Ohad Yossef Hay et al., "Pulse Oximetry with Two Infrared Wavelengths without Calibration in Extracted Arterial Blood", MDPI Journal, Sensors 2018, 18, 3457, pp. 1-13.

NONIN Technical Bulletin, "The Effects of Dark Skin Pigmentation and Low Saturation in Oximetry" "NONIN PureSAT® Oximetry Technology Provides Superior Accuracy in the Most Challenging Environments", Technical Bulletin, Feb. 2008.

Amy Moran-Thomas, "How a Popular Medical Device Encodes Racial Bias" Boston Review, COVID-19, Health, Race, Science and Technology, Aug. 5, 2020.

Santiago Lopez, "Pulse Oximeter Fundamentals and Design", NXP Freescale Semiconductor Application Note, Document No. AN4327, Rev. 2, Nov. 2012.

* cited by examiner

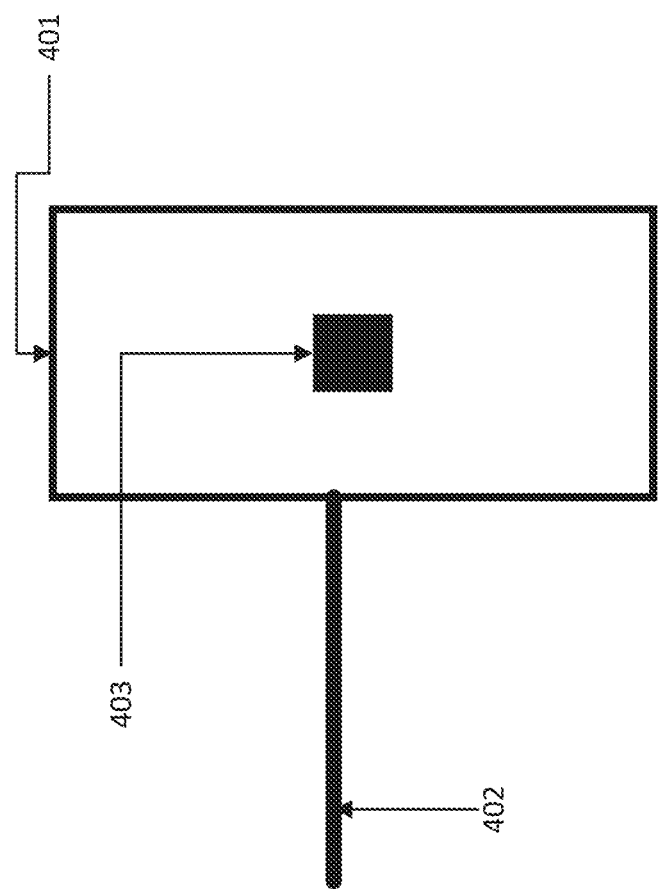

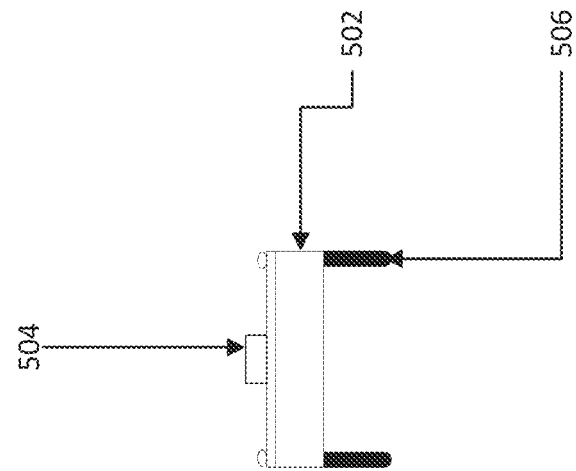
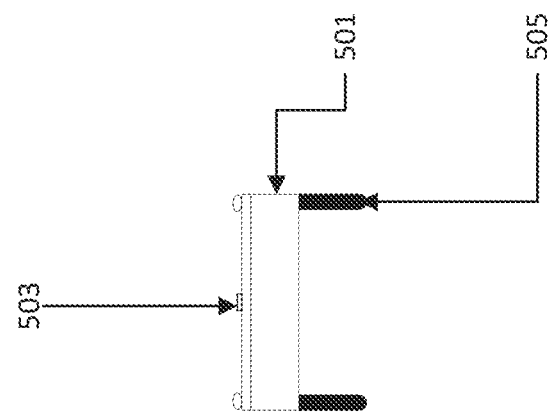

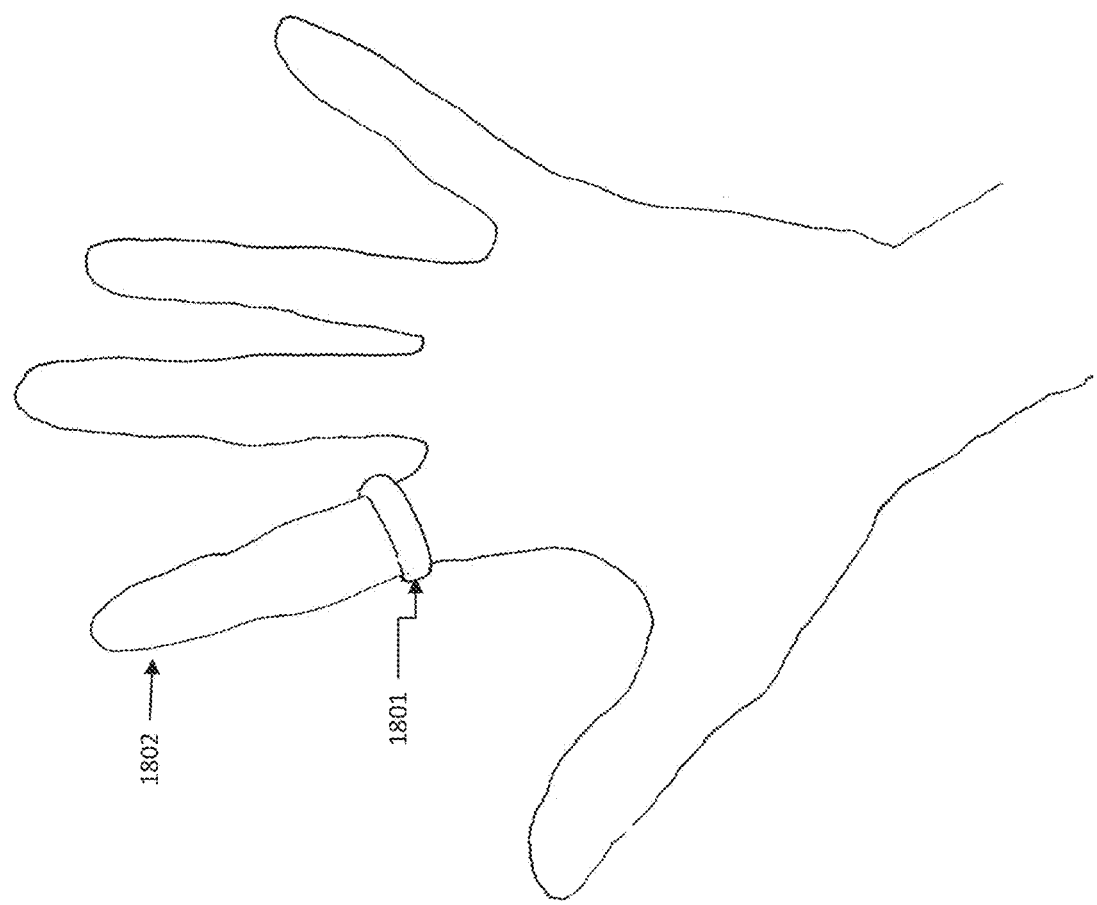

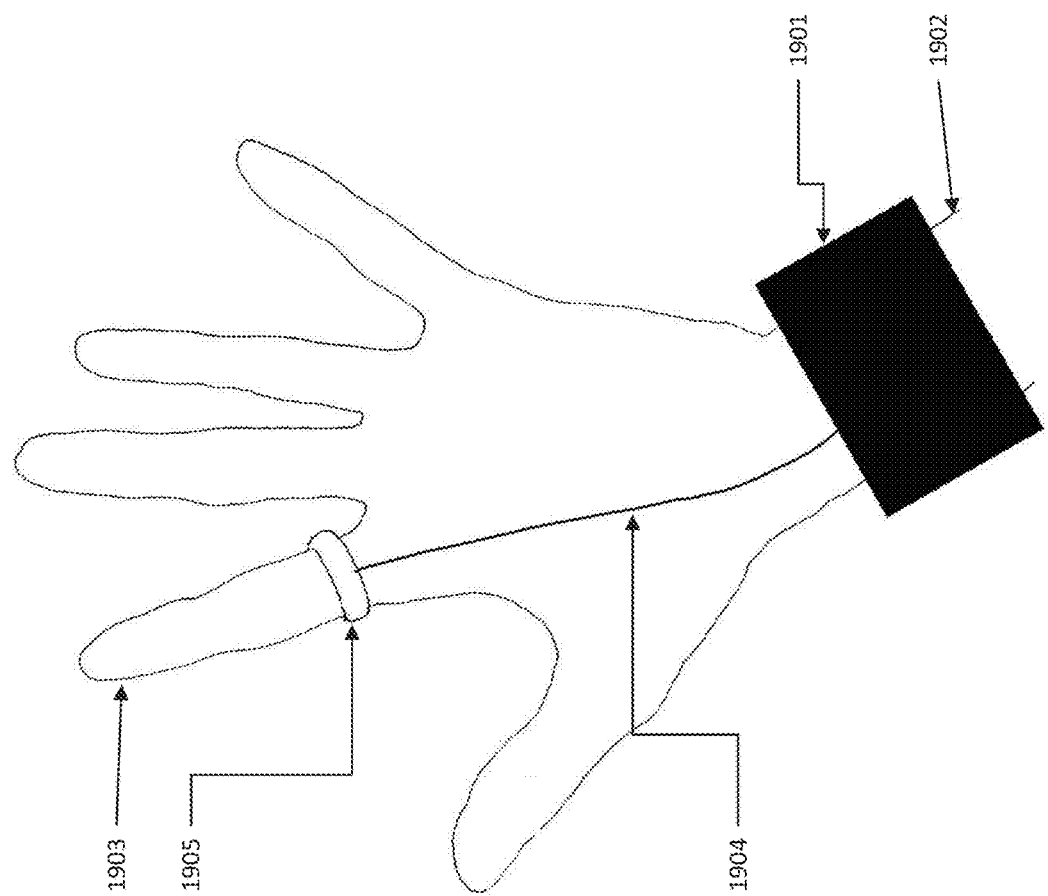

MELANIN-BIAS REDUCING PULSE OXIMETER AND PATIENT MONITORING SYSTEMS AND DEVICES

CROSS-REFERENCE TO RELATED APPLICATION

This application claims benefit of priority from U.S. Provisional Application No. 63/230,815 filed on Aug. 9, 2021, the entire contents of which are incorporated by reference.

TECHNICAL FIELD

The technology relates to pulse oximeters, heart rate monitors, EKG systems, and other patient monitoring devices. More specifically, the technology relates to hardware, software, integrated circuits and components that create pulse oximetry that is not biased toward melanin, as well as its accompanying user interface, patient monitoring integration, and wireless technology.

BACKGROUND

There are currently pulse oximeters on the market that allow for heart rate, pulse oximetry and plethysmograph (pleth) graph data to be presented to the user, via on-board display, wireless technology, smart device, or patient monitoring system displays. These pulse oximeters operate as stand-alone devices, networked, and/or wireless devices. Displays used for these pulse oximeters are either light emitting diode (LED) arrays/matrices, liquid crystal displays (LCDs), or organic light emitting diodes (OLEDs). These pulse oximeters use two different wavelengths of LEDs to operate. One LED is a red LED normally in the 640 nm range, and the other LED is an IR LED normally in the 940 nm range. Some pulse oximeters use red and IR LED combinations in other, but similar wavelengths. These pulse oximeters use the data from both LEDs, via a photodiode, in order to calculate the blood oxygen saturation level in a patient. The heart rate is calculated by using the data from only one LED, typically the IR LED. It is possible to get a blood oxygen saturation reading, via these two LEDs, because these LEDs' wavelengths are on opposite sides of the isosbestic point of the absorption rates for oxyhemoglobin and deoxyhemoglobin for these wavelengths. The isosbestic point is the specific wavelength at which the total absorption of a material does not change during a physical change in the sample. In the case of hemoglobin this is the point where the absorption rates of oxyhemoglobin and deoxyhemoglobin are the same. Oxyhemoglobin is the oxygenated hemoglobin in the blood, and deoxyhemoglobin is the deoxygenated hemoglobin in the blood.

The problem experienced by many of these pulse oximeters is that the red light is absorbed and scattered by melanin that resides in the skin, and provides falsely high blood oxygen saturation readings on patients with skin containing higher concentrations of melanin. Melanin is a dark brown or black pigment in skin that is also responsible for tanning when exposed to sunlight. The darker the skin, the larger the concentration of melanin, and therefore, a higher amount of melanosomes, where melanosomes are the lipid bilayer bound organelle that produces melanin. Absorption occurs when light or photons are completely blocked from passing through the materials in question due to the materials "taking in" the light or photons. Scattering occurs due to the bouncing of light or photons at incident angles due to the contacting of the material or object in question. The melanin and melanosomes both contribute to the light disruption, via absorption and scattering. It has also been found that the lipid bilayers scatter light depending on the concentration of the bilayers and the intensity and type of the incoming light.

Overall scattering occurs at a higher rate at lower wavelengths, although scattering does occur across the light spectrum. Absorption, however mainly occurs in the melanin found in the epidermis mostly located in the basal layer where high concentrations of melanosomes are found. The two types of melanin that pose the largest absorption problem are pheomelanin and eumelanin, which have different effects on skin color and therefore cause different wavelengths to be absorbed at different rates. Pheomelanin portrays a red/yellow color, while eumelanin portrays a brown/red color. Therefore, in current pulse oximeters that use red light, although pheomelanin causes absorption problems, eumelanin causes a higher rate of absorption and therefore a higher rate of falsely high pulse oximetry readings. Eumelanin concentration is directly proportional to the shade of skin color and is mostly responsible for the overall darkness of the skin, where pheomelanin has a more constant trend across the shades of skin color and is primarily responsible for the yellow/red tint in skin color. Therefore, the shade of skin color is directly proportional to the concentration of eumelanin in the skin, and is the type of melanin that is responsible for the greatest bias causing falsely high blood oxygen saturation readings.

The user interface for many pulse oximeters is a single-color output that can be difficult for non-medical patients, laypersons, or personnel to interpret blood oxygen saturation levels. These screens often have a single low battery indicator that does not accurately display the remaining battery life of the meter. Also, many meters often use disposable batteries, rather than rechargeable batteries.

Many pulse oximeters currently on the market use a design that clips onto fingers or toes and can be cumbersome to wear for extended periods of time. On patients with poor circulation, the meters are currently taped or clipped onto the ear, which is not an ideal placement and the cables can become a hazard to the patient. For infants, the meters are often taped or wrapped around a leg or wrist. For toddlers, the meters are often taped or wrapped around a finger or toe because the meters currently on the market do not accommodate smaller appendages. These meters often fall off and can also reduce the accuracy of the blood oxygen saturation and heart rate readings and results. In many cases, the meter designs previously mentioned, are extremely sensitive to patient movement, which can result in inaccurate readings as well. These designs at best are water resistant and not waterproof, posing a problem for patients that must wear these meters for extended periods of time.

Some newer pulse oximeter designs utilize non-flexible rings which cause these meters to be ineffective when used on individuals with smaller fingers and/or toddlers/infants. Also, some designs utilize IR LEDs to measure pulse oximetry readings using the patients' foreheads and lack the comfort and other features that the invention discussed in this document provides.

SUMMARY

The invention solves many of the issues mentioned in the background section, via different means depending on the embodiment. One example embodiment of the invention uses the finger clip design, in either a standalone or connected patient monitoring system, similar to the physical designs currently on the market, however, utilizing the melanin bias reducing blood oxygen saturation measurement method herein. Another example embodiment uses a flexible ring design, and another example embodiment uses a flexible bracelet design to alleviate many of the placement concerns noted with the current pulse oximeters on the market. An example embodiment of the ring design uses material and casing to ensure waterproof operation. The ring and bracelet embodiments are sized, depending on application, to work for both infant monitoring on wrists or legs, as well as adult and pediatric monitoring on fingers. The ring and bracelet embodiments' sizing also allows for ease of use for patients who may be amputees or patients who are unable to wear traditional pulse oximeters for reasons such as for example, but not limited to, anatomy, age, mental disability, sensitivity issues, and/or ADD. Example embodiments of the ring and bracelet embodiments include, but are not limited to, an embodiment with a built-in screen, an embodiment with a smart device display, an embodiment with a wrist mounted screen, and/or an embodiment connected to a patient monitoring system. Further, other example embodiments of the bracelet are designed in such a way that they incorporate a wearable flexible band.

One example embodiment of the invention reduces the melanin issue previously discussed by using 2 IR LEDs, about 768 nm and about 940 nm, along with an analog photodiode and accompanying analog circuits and software. Another example embodiment of the invention uses a digital photodiode, along with accompanying software to solve this problem. Yet another example embodiment of the invention uses a phototransistor, along with accompanying hardware and software to solve this problem. In order to determine the best LEDs and detectors (analog/digital) to use, one example embodiment of a test bench system is used. This example embodiment of the test bench system uses serial dilutions of synthetic melanin used to dye pig skin to represent different concentrations of melanin in human skin. In this example embodiment, the test bench measures the intensity of light received, after passing through different concentrations of melanin dyed pig skin, through a variety of different tests.

One example embodiment of the invention uses a user interface that displays pleth graph, blood oxygen saturation level, heart rate, and battery meter. One example embodiment of the screen layout changes color when the pulse oximeter detects good (95-100%), moderate (90-95%), or critical (<90%) blood oxygen saturation level readings to increase ease of use and help with blood oxygen saturation level interpretations especially when used by a layperson. Another example embodiment of the screen layout uses a segmented battery meter that changes color to indicate a good battery, almost discharged battery, and battery that needs to be recharged after the next few uses.

One example embodiment of the invention uses disposable batteries as its power source. Another example embodiment uses rechargeable batteries. Further, another example embodiment uses a wall adaptor, such as, for example, in hospital patient monitoring systems. Further, another example embodiment uses a wall adaptor with a built-in battery backup, such as, for example, in other hospital patient monitoring systems. These example embodiments use many different types and styles of batteries depending on the embodiment and its space, weight, and power consumption requirements.

One example embodiment uses wireless technology for the pulse oximeter to communicate with the user interface. This wireless interface takes on many different embodiments. An example embodiment is a system that wirelessly communicates directly with a patient monitoring system. Yet another example embodiment communicates with a belt or wrist-pack that contains a small user interface and boosts the wireless signal to be transmitted to the hospital patient monitoring system. Further, another example embodiment communicates with a patient monitoring system via wired and wireless networked communications. These wireless and wired embodiments are compatible with all embodiments of the pulse oximeter design, in accordance with the invention.

Another example embodiment of the design includes heart telemetry monitoring built into the pulse oximetry system therefore providing a $5^{th}$ vital sign as a blood oxygen saturation level to the patient monitoring system. An example embodiment of this includes skin electrodes that are wired to a belt or chest pack that combines this information with the pulse oximetry system (wired or wireless) to be displayed locally or transmitted (wired or wireless) to the patient monitoring system. Another example embodiment of the heart rate telemetry system includes skin electrodes that use individual wireless transmitters rather than their wired electrodes to transmit heart rate data along with the pulse oximetry data to either a local belt pack, a bedside monitor, or directly to the patient monitoring system, thus being able to discard cumbersome cables on the patient. Another example embodiment of the heart rate telemetry system uses a waterproof centralized controller, which can be adhered to the patient's chest or other location near the heart, and combines the information from the skin electrodes, via short cables, with the pulse oximeter reading to be displayed wired or wirelessly locally, or wired or wirelessly via the patient monitoring system.

BRIEF DESCRIPTION OF THE DRAWINGS

FIG. 4 shows an example embodiment of a general layout, in accordance with the invention, of an example embodiment of a digital detector for a test bench system.

FIG. 5A-5B shows an example embodiment of two example LEDs and their example mounting and connection methods, in accordance with the invention, for a test bench system.

FIG. 18 shows a diagram of an example usage of an example embodiment of a ring design of a pulse oximeter, in accordance with the invention.

FIG. 19 shows a diagram of an example usage of an example embodiment of a ring design of a pulse oximeter, in accordance with the invention, including an example embodiment of a UI (user interface).

DETAILED DESCRIPTION

Systems, in accordance with the invention, include a pulse oximeter device that includes a method for reducing the melanin bias in skin. This pulse oximeter system includes multiple methods for receiving the telemetry, including heart telemetry, and blood oxygen saturation information, wired or wirelessly, through a user interface, for example a patient monitoring system or standalone UI. There are multiple embodiments of this pulse oximeter system that take on different forms, shapes, and attachment methods. Part of the development of this pulse oximeter system included using a testing system for determining the best optical configuration and design for reducing the melanin bias discussed previously in this document.

Test Bench

The test bench is a system that was developed for determining the best optical arrangement to reduce the melanin bias that causes light absorption and light scattering to interfere with accurate pulse oximetry readings. The test bench consists of hardware, software, and physical components, such as, for example, pig skin and synthetic melanin dye. The example embodiment discussed in this section was developed using perf board, as well as through-hole parts, including SMD components mounted onto through-hole converter PCBs. Other example embodiments of the test bench are constructed using custom PCB's and primarily SMD parts to reduce the size and increase the robustness of the device.

Figure 1:
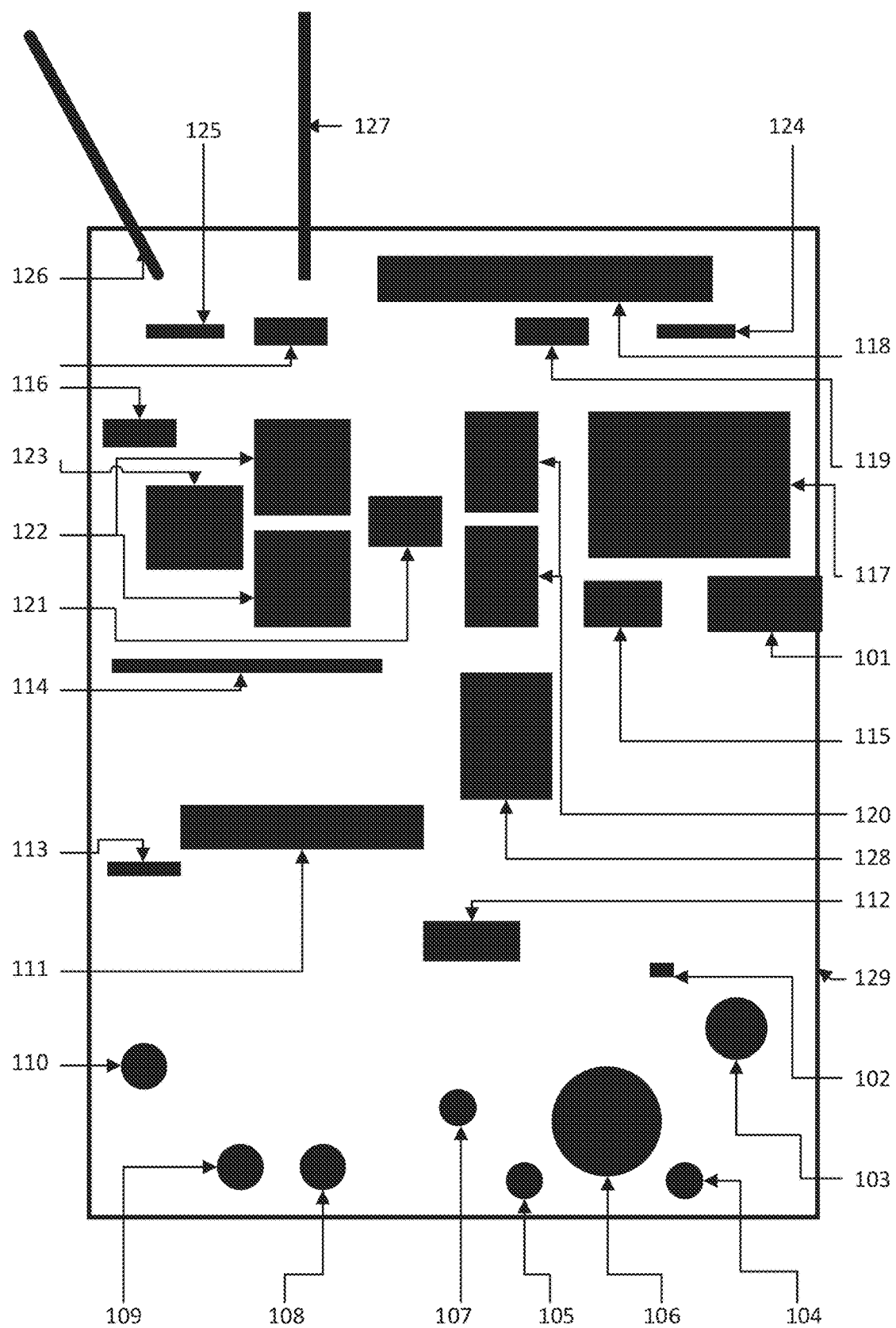
FIG. 1 shows an example embodiment of a general hardware layout of an example embodiment of a test bench system, in accordance with the invention, used for performing LED and detector performance tests to achieve a(n) LED(s) and a detector combination to reduce the melanin bias.

FIG. 1 shows an example embodiment of a general hardware layout of an example embodiment of the test bench system showing general locations of the hardware components. 101 represents the power input barrel adaptor used to connect an AC wall adaptor to power the circuit. Other example embodiments use USB connectors and a USB power source, instead of a barrel jack for 101.

Furthermore, other example embodiments of the test bench use other power sources, including but not limited to, on-board AC/DC converters and/or batteries. 102 represents the header jumper to disable or enable the buzzer output part of the user interface. Other example embodiments of the test bench use digital or analog methods to control the buzzer, including, but not limited to, GPIO controlled switching methods. 103 represents the buzzer part of the user interface that emits sound based on user input and program actions. Other example embodiments of the test bench use other forms of audio and/or visual indicators instead of a buzzer, such as, but not limited to, speakers or audio and/or voice synthesizers. The user input block consists of 104-107. 104 represents the tactile switch used for moving right by one digit on display 201. 105 represents the tactile switch used for moving left by one digit on display 201. 106 represents the rotary encoder used to move through digits on display 201 and to detect enter presses. 107 represents the menu select button used to move through different menus on LCD screen 201. The user input block in other example embodiments consists of other input methods, such as, but not limited to, multiple rotary encoders, touch screens, keyboards, keypads, and/or computer and smart device interfaces. The LCD control block consists of 108-109. 108 represents the display, 201, brightness adjustment potentiometer. 109 represents the display, 201, contrast adjustment potentiometer. In other example embodiments, the LCD control block is replaced with other analog or digital methods of control, including, but not limited to, fixed resistor values, GPIO control, digital potentiometer control, and/or digital to analog converter control (DAC). Other example embodiments in which different types of displays, 201, are used have different control blocks, 108-109, depending on the display technology used. 110 represents the microcontroller, 111, reset button to reset the microcontroller in case of a program halt. Other example embodiments replace the reset button with watch dog timers. 111 represents the MCU (microcontroller unit). In the example embodiment shown, an Atmel ATM EGA 328P is used for the MCU 111. Other example embodiments of the test bench use other types of microcontrollers with similar features and functions. 112 represents the crystal oscillator used as the clock for MCU 111. In the example embodiment of the test bench discussed here, 112 is a 16 MHz clock, in order to allow for proper software performance. 113 represents the programming header used for reprogramming MCU 111. 114 represents the alpha numeric LCD screen header that the screen 201 attaches to. Other example embodiments of the test bench use other methods of attachment depending on the display type used. 115 represents the fusing block used to protect the test bench in the event of a short. 116 represents the power regulation block that produces both the 3.3V and 5V source required to power the test bench. Other example embodiments of the invention use other voltage sources and power supply methods to power the test bench. 117 represents the current monitoring control block, which is connected to current shunt 118 for calibration purposes. 119 represents the calibration controller used to calibrate the current meter 117 during initial boot-up. 120 represents the LED current driver block used in conjunction with 121 and 122 to create a current source for the LEDs used in testing. 121 represents the op-amp, placed in comparator mode, and is part of the current source. 122 represents the DAC section of the current source. Other example embodiments use other methods for the DAC portion of the current source that generates a programmable voltage output including, but not limited to, PWM filtered analog voltages. Further, other example embodiments use other methods to produce a controllable current source for the LEDs, such as, but not limited to, current source ICs, digitally controllable regulators, or digitally controllable current source supplies. 123 represents the level shifter block for the digital detector, 203. Other example embodiments of the test bench use other types of digital detectors that do not require voltage level shifting at block 123. 124 represents the analog detector, 204, connector and 125 represents the digital detector, 203, connector. One example embodiment of these connectors, 124 and 125, is a header style connector. Other example embodiments of connectors 124 and 125, include, but are not limited to, Molex connectors, ZIF connectors, gold fingers, ribbon cable connectors, and/or JST connectors. 126 represents the main LED cable and 127 represents the secondary LED cable. Other example embodiments use other methods for attaching LEDs to the test bench system, including, but not limited to, snap connectors, JST connectors, headers, barrel jacks, Molex connectors, and/or butt connectors. 128 represents the reverse current protection control block of the circuit to protect the testing system from inadvertent inverse polarity power supplies connected via barrel jack, 101. 129 represents the main board that all components previously discussed for the test bench are mounted to. One example embodiment of the main board is perf board with a plastic cover to protect the solder joints. Another example embodiment of the main board is the printed circuit board (PCB) with a plastic cover to protect the traces.

Figure 2:
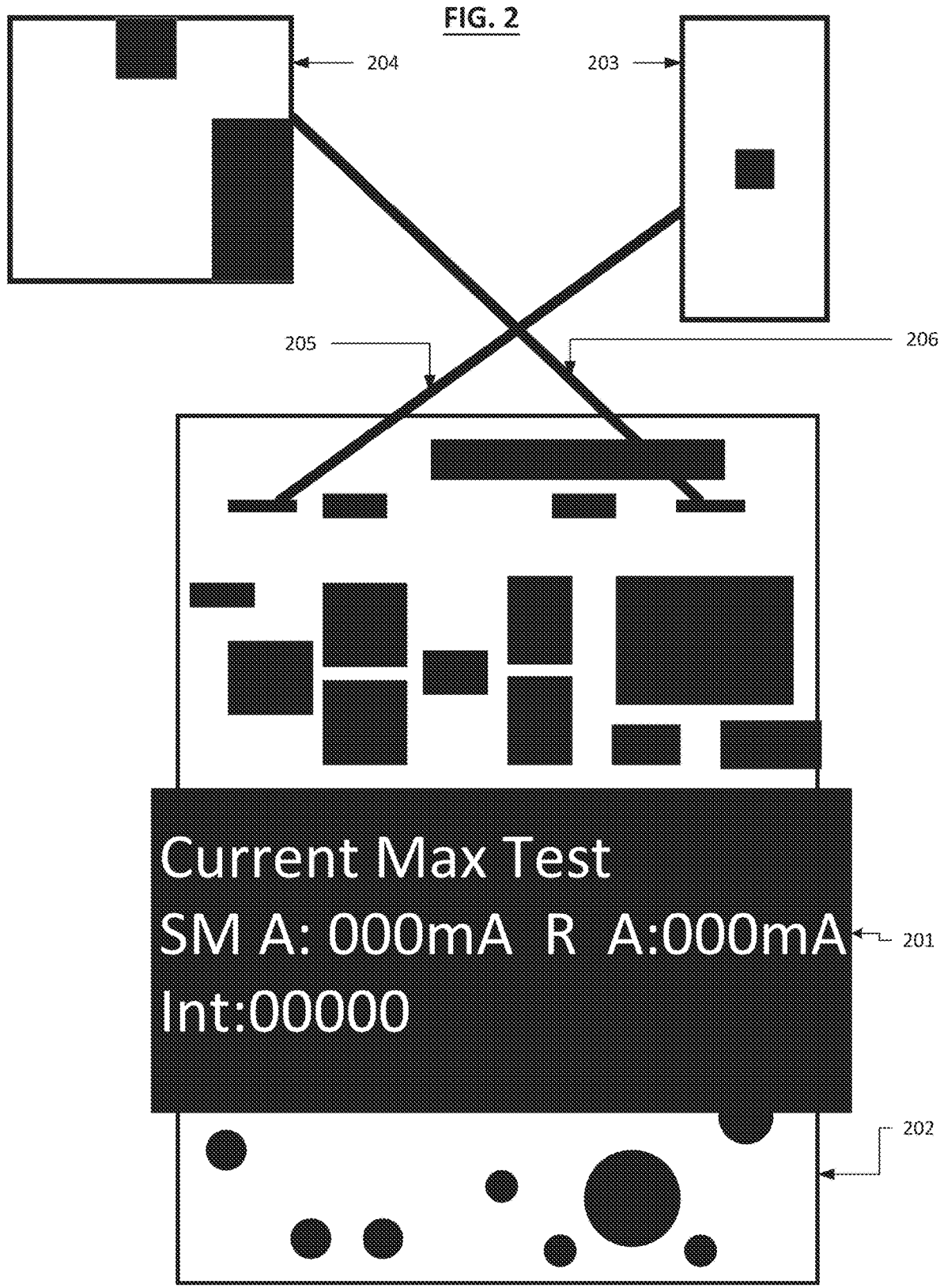
FIG. 2 shows an example embodiment of a test bench system including its UI and peripheral interface devices used for testing, in accordance with the invention.

FIG. 2 shows an example embodiment of the test bench system including its user interface and detectors. 201 represents the alpha numeric screen mounted on the test bench. Other example embodiments of the test bench use other display methods for screen 201, such as, but not limited to, LCD, OLED, E-ink, computer display, and/or smart device display. 202 represents the main board as described before (board 129). 203 represents the digital detector described further in FIG. 4. 204 represents the analog detector described further in FIGS. 3. 205 and 206 represent the ribbon cables that provide power and data transmission for the digital and analog detectors respectively. Other example embodiments of the test bench system use other connection methods instead of ribbon cables 205 and 206, such as, but not limited to, FPC cables, multi-core cables, and/or twisted pair cables.

Figure 3:
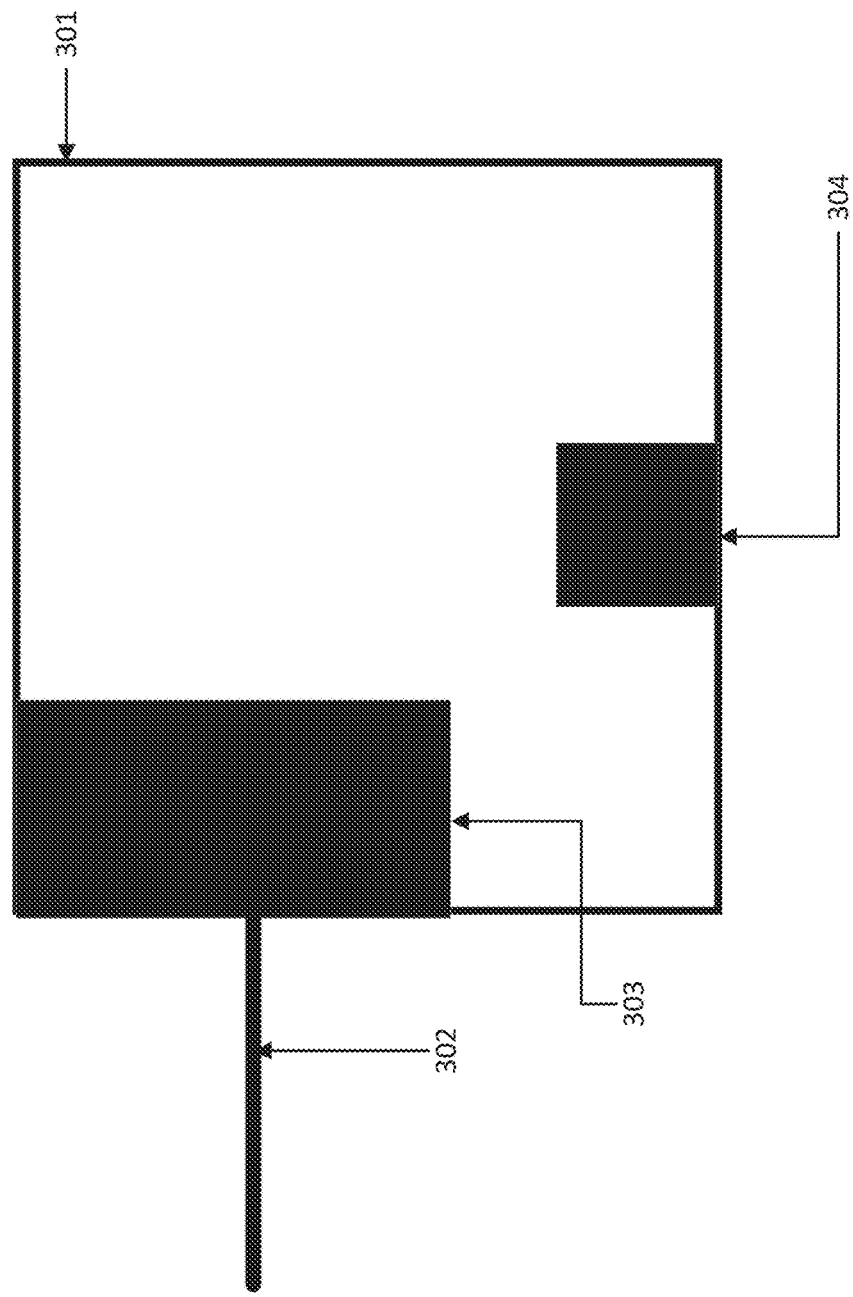
FIG. 3 shows an example embodiment of a general layout, in accordance with the invention, of one example embodiment of an analog detector for a test bench system.

FIG. 3 shows an example embodiment of a general layout of the analog detector circuit. 301 represents the main analog detector board. In the example embodiment shown, board 301 is a piece of perf board using through-hole parts. Other example embodiments of the test bench use SMD parts and custom PCBs for board 301. 302 represents the cable discussed as 206 in FIG. 2. 303 represents the high-resolution analog to digital converter (ADC) which converts the voltages from photodiode 304 to data for MCU 111. 304 represents the photodiode with a built-in transimpedance amplifier. A transimpedance amplifier is required to convert the low current signals produced by the photodiode into voltages useable by the ADC, 303. Other example embodiments of the analog detector circuit use separate analog photodiodes and transimpedance amplifiers instead of the all-in-one IC shown in 304. Other example embodiments of the analog detector circuit use separate analog phototransistors instead of the all-in-one IC shown in 304.

FIG. 4 shows an example embodiment of a general layout of the digital detector circuit. 401 represents the main digital detector board. In the example embodiment shown, board 401 is a PCB using SMD parts. Other example embodiments of the test bench use perf board and through-hole parts or other SMD parts and custom PCB designs for board 401. 402 represents the cable discussed as 205 in FIG. 2. 403 represents the all-in-one digital photodiode which produces a digital output representing the light for MCU 111 to use. Other example embodiments of the digital detector circuit use other digital light and intensity detection methods instead of the all-in-one IC shown in 403.

FIG. 5A and FIG. 5B are example embodiments of LEDs and example mounting and connection methods. 501 and 502 represent mounting boards for SMD LEDs. 503 and 504 represent example SMD LEDs of different sizes. 505 and 506 represent the electrical connection pins for the LED mounting systems. Other example embodiments use other sizes and styles of both SMD and through-hole LEDs, as well as other sizes and styles of mounting methods for these LEDs. Multiple sizes of LEDs are tested to determine if LED surface area and light output angle have an effect on the reduction of the melanin bias during testing.

Figure 6:
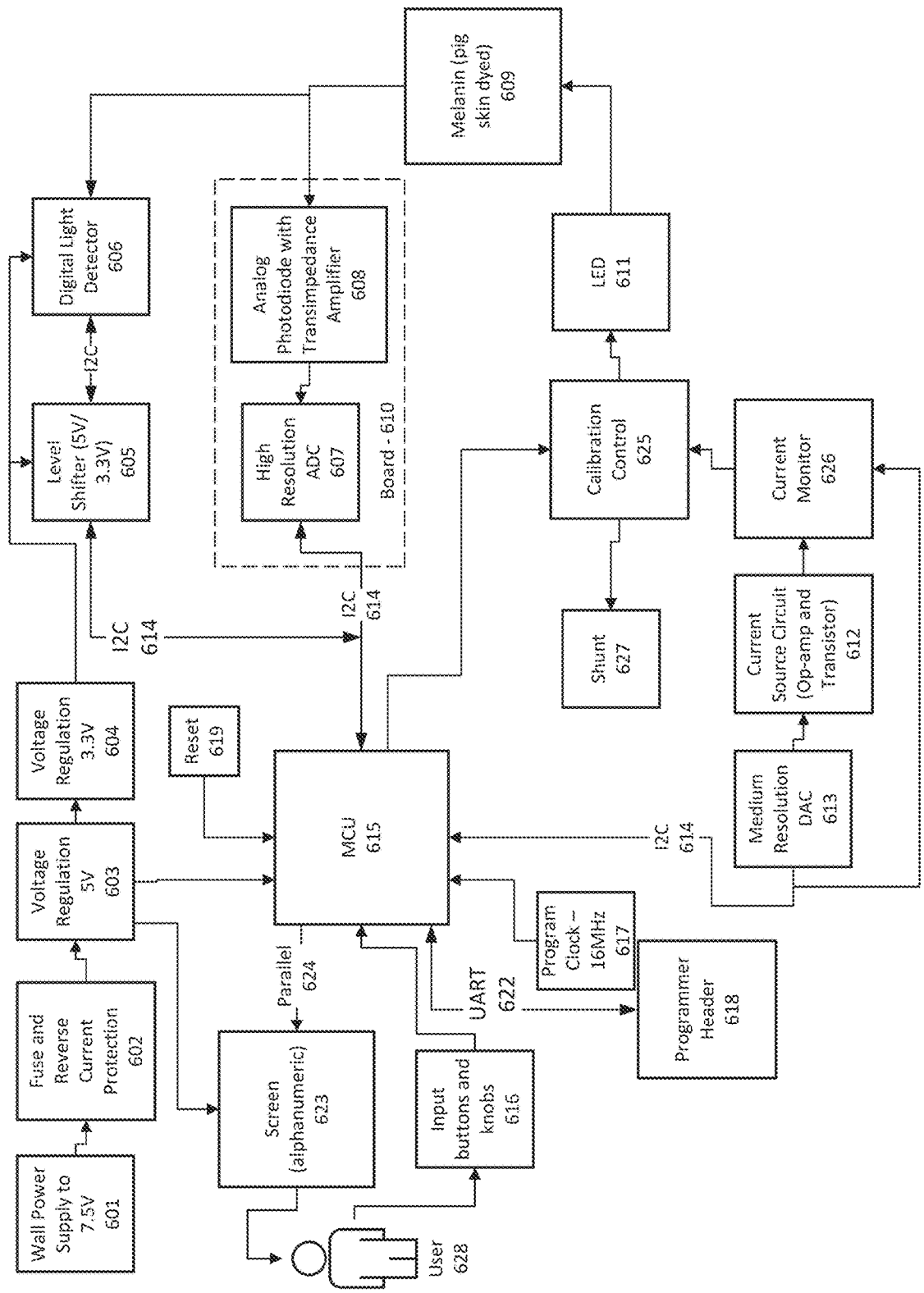
FIG. 6 shows an overview of a general hardware signal flow of an example embodiment of a test bench system, in accordance with the invention.

FIG. 6 shows an overview of a general hardware flow of an example embodiment of the test bench system. 601 is the wall power supply that connects through barrel jack 101 to give power to the circuit. Other example embodiments of the test bench system use other power methods instead of wall adaptor 601, such as, but not limited to, mains supply through AC/DC converters, USB power, and/or batteries. Block 602 is the fusing and reverse current protection, also 115 and 128 respectively. In the example embodiment shown, a PTC fuse is used so the device is easily resettable, and a metal-oxide-semiconductor field-effect transistor (MOSFET) with a diode is used for reverse current protection. Other example embodiments of the test bench system use other styles of fuses, such as, but not limited to, glass or blade fuses and use other forms of reverse current protection, such as, but not limited to, dedicated reverse current protection ICs or single diode methods. 603 and 604 are the 5V and 3.3V regulation blocks respectively, also shown in 116. Other example embodiments of the test bench system use other voltages and/or voltage regulation methods depending on the circuit requirements for those embodiments. 605 is the 5V to 3.3V level shifter for the I²C data stream for the digital detector 606. Level shifter 605 is also shown in 123. Other example embodiments of the test bench system use other types of level shifters depending on the voltage requirements, and other example embodiments do not require a level shifter for I²C data for digital light detector 606. 606 is the digital light detector, also shown in FIG. 4. In the example embodiment shown, a TSL2591 I²C light detector is used. Other example embodiments of the test bench system use other types of digital light detectors. 607 is the high-resolution ADC, also shown as 303. In the embodiment shown a 16-bit I²C ADS1115 is used. Other example embodiments of the test bench system use other forms of analog converters. It is important that the analog converter has a high enough resolution so that it is able to detect the minute differences between the absorption of oxyhemoglobin and deoxyhemoglobin when transferred for use in the pulse oximeters discussed later in this document. 608 is the analog photodiode, also shown as 304. In the example embodiment shown, an OPT101 was chosen for this part, since it includes a transimpedance amplifier, which makes the overall design require less components. Other example embodiments of the test bench system use other types of analog photodiodes for 608, some of which require an independent transimpedance amplifier circuit. A transimpedance amplifier is required to convert the small currents produced by the photodiode into readable voltages for the ADC 607 to use. In other example embodiments of the test bench system, ADC 607 is internal to MCU 615. 609 is the melanin dyed pig skin. The melanin dyed pig skin is used to simulate different concentrations of melanin in human skin for testing purposes. 610 is the board 301 that both 607 and 608 mount to. 611 is the LED, for example, 503 and 504. During testing many different LEDs are used to find the best option to reduce the melanin bias for the pulse oximeter discussed later in this document. 612 is the op-amp and transistor portion 121 and 120 of the current source circuit. 613 is the DAC 122 portion of the current source circuit. Other example embodiments of the test bench system use other methods to create a digitally controlled variable voltage source for op-amp and transistor 612, such as, but not limited to, PWM with filtering, and/or digital potentiometers. In other example embodiments of the test bench system, DAC 613 is internal to MCU 615. Further, other example embodiments use other methods to produce a controllable current source for the LEDs, such as, but not limited to, current source ICs, digitally controllable regulators, or digitally controllable current source supplies. I²C signal 614 is used to interconnect all of the devices (digital light detector 606, high resolution ADC 607, DAC 613, and current sensor 626) with the MCU 615. MCU 615 (also 111) is where the main program is stored and executes its functions based on user input 628, via buttons and knobs 616 also 104-107. In the embodiment shown MCU 615 is an Atmel ATMEGA 328P microcontroller clocked at 16 MHz, via the crystal oscillator program clock 617 (also 112). Other example embodiments of the test bench system use other types of microcontrollers and other types of program clocks running at other speeds. 618 is programming header 113, which is attached to a computer in order to update the program stored in MCU 615, via UART signal 622. Other example embodiments of the test bench system use other programming methods, such as, but not limited to, ICSP, SWD, SPI, J-TAG, and/or wireless methods. Furthermore, other example embodiments of the test bench system use the programming header in order to communicate with a computer or smart device as part of its user interface. 619 is reset button 110. Other example embodiments of the test bench system use a watch dog timer for 619 to automatically reset the MCU in the event of a program hang. 623 is the alpha numeric screen (also 201) portion of the user interface that presents information to user 628, while the test bench system is running. In the example embodiment shown, screen 623 is connected to MCU 615, via parallel interface 624. Other example embodiments of the test bench system use other types of interfaces to connect between MCU 615 and screen 623 such as, for example, SPI, I²C, 1-wire, and other serial methods. Furthermore, other example embodiments of the test bench system use other types of screens for 623, such as, but not limited to, LCD, OLED, LED array, touch screen, and/or computer or smart device interfaces. 625 and 627 (also 119 and 118) are the calibration controller and current shunt, which calibrates the current sensor 626 on initial boot up. This calibration accounts for voltage drift as parts wear out and become less efficient or if different voltage inputs occur due to mains fluctuation. Current sensor 626 (also 117) in the embodiment shown is an INA219 I²C current sensor. In other example embodiments of the test bench system, other current sensors and current sensing methods are implemented. User 628 controls the test bench system, via input buttons and knobs 616 (also 104-107) and receives data back from the test bench system, via screen 623. User 628 also switches out different concentrations of melanin dyed pig skin 609, as well as different LEDs, 611, and detectors, 606 and 608, to test.

Figure 8:
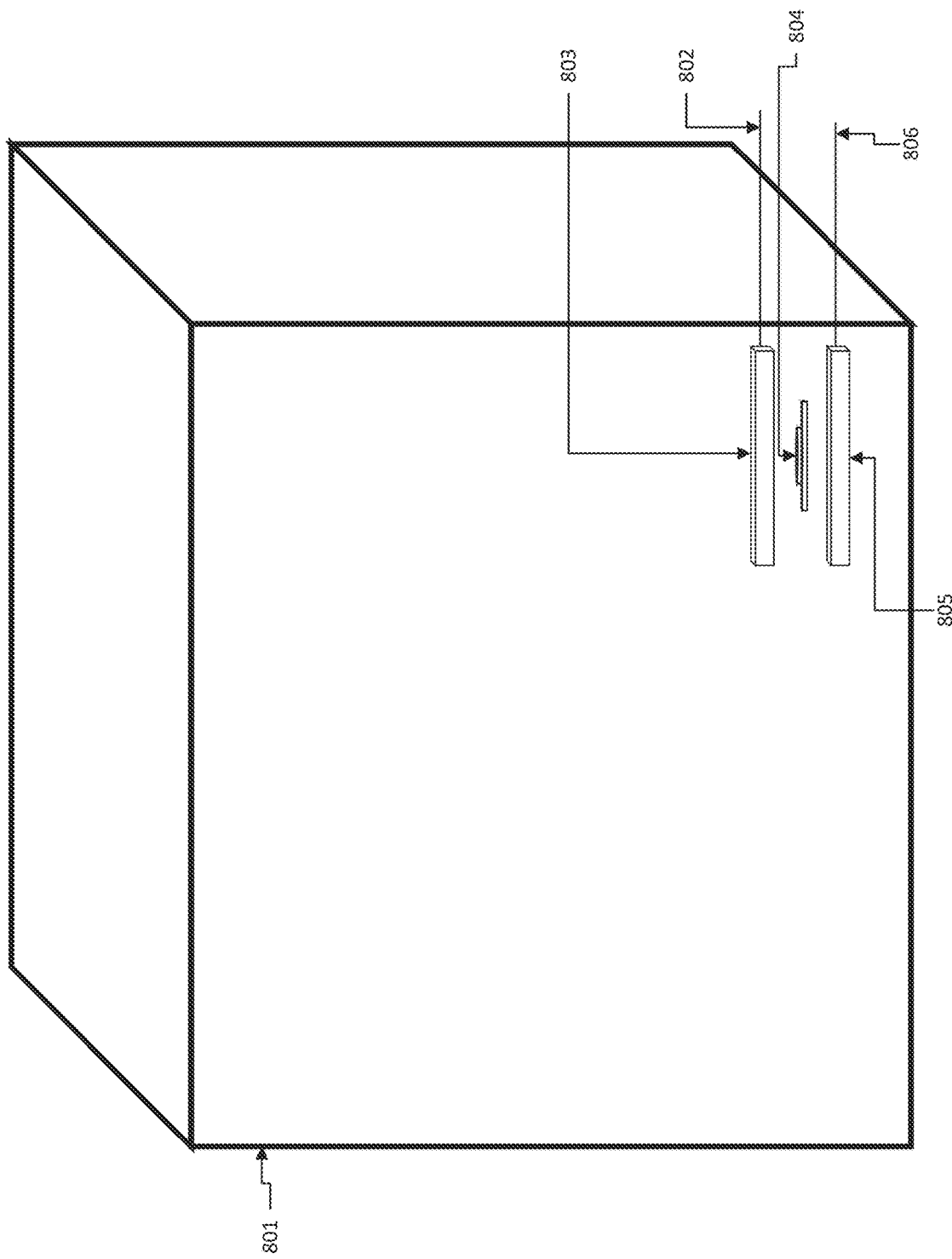
FIG. 8 shows a general usage method, in accordance with the invention, of an example embodiment of a test bench system with pig skin, detector, emitter, and a blackout box.

The signal interaction and flow shown, in the example embodiment in FIG. 6, works as follows. User 628 selects the LED 611 to start testing, as well as which detector to start testing with, digital 606 or analog 608. The user 628 places the melanin dyed pig skin 609 between the LED 611 and the detector 606 or 608 and places this setup in a blackout box, 801, to prevent interference from ambient light, as shown in FIG. 8. The user 628 uses input buttons and knobs 616, as well as user interface screen 623 to select menu options, tests, and values to be used in the testing process. Microcontroller 615 clocked, via the program clock 617, runs firmware instructions per user 628's input requests and returns these results to screen 623. Microcontroller 615 controls screen 623, via parallel interface 624, which is controlled by the screen drivers which are part of the firmware on microcontroller 615. Microcontroller 615 controls DAC 613, high resolution ADC 607, current sensor 626, and digital light detector 606, via the I²C bus 614. DAC 613's output voltage is sent to op-amp and transistor 612, configured in comparator mode to create a current source that controls LED 611, and is monitored by current sensor 626. Light from LED 611 passes through pig skin 609 and enters either a digital light detector 606 or analog photodiode 608 depending on user 628's input selection. Analog photodiode 608 contains a built in transimpedance amplifier in the example embodiment shown, which sends its voltage output signal to ADC 607 to return a digital intensity value to MCU 615. Other example embodiments use phototransistors instead of photodiode 608. Further, other example embodiments use, for example, an analog photodiode 608 with external transimpedance amplifier circuits. If user 628 selects a digital input method, digital light detector 606 sends its digital intensity data to microcontroller 615 over I²C bus 614, via level shifter 605. Other example embodiments use other digital light detection methods and communication methods instead of digital detector 606. Microcontroller 615 controls calibration circuit 625, which when enabled, diverts current from LED 611 to current shunt 627, which allows for known current values to be returned based on the fixed resistor value of the current shunt 627, in order to calibrate DAC 613 and current source circuit 612. Programming header 618 is used to program/update firmware on MCU 615 over UART interface 622. Power for all circuits is generated via 5V regulation 603 which receives its power from wall supply 601 via fuse and reverse current protection 602. Light detector 606 requires voltage level shifting 605 and receives its power, via 3.3V regulation 604, which receives its power, via 5V regulation 603. Other example embodiments of hardware flow are used in other embodiments of the test bench system, in accordance with the invention, via other example signal paths and circuits.

Figure 7:
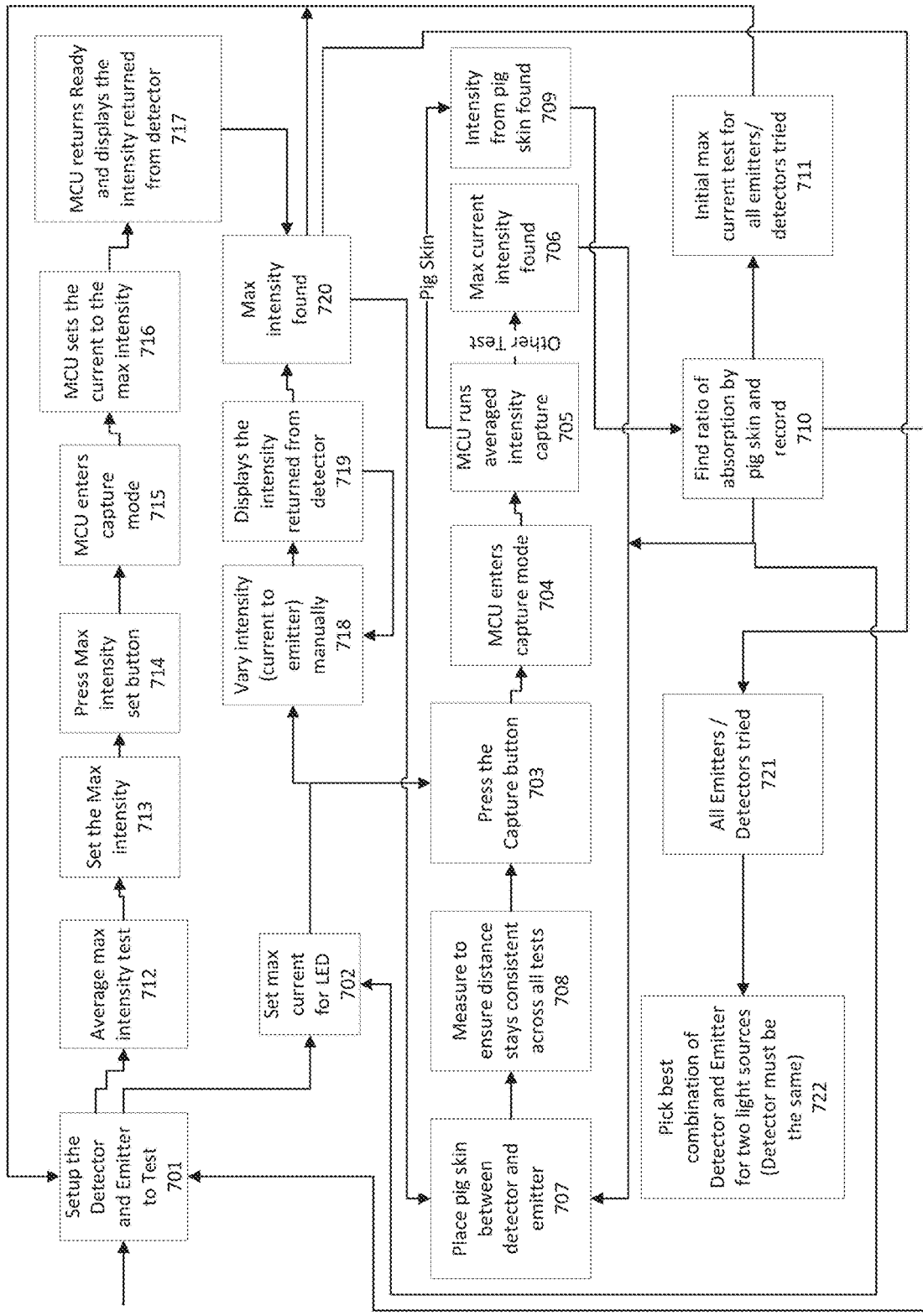
FIG. 7 shows an overview of a general usage, via the UI (user interface), in accordance with the invention, of an example embodiment of a test bench system.

FIG. 7 shows an example of a general usage of an example embodiment of a test bench used to find the best LED and detector combination for a method of measuring blood oxygen saturation that reduces the melanin bias, via an example user interface. In block 701, the user sets up the detector and emitter to start testing with, as shown in FIG. 8. The user starts the example usage process by setting the max current for the LED 702. The user presses the capture button 703, in order to begin the max current test, which is used to determine the maximum returned intensity for all emitters to have a comparison point. The MCU (also 111 and 615) enters capture mode 704. After capturing the intensity from the detector, the intensity values across the time span of the capture are averaged in block 705. Max current intensity found is returned to block 706. The user, following the example diagram in FIG. 8, places the pig skin between the detector and emitter 707. The user measures the distance, as described in FIG. 8, to ensure the distance stays consistent in all tests in block 708. The user performs blocks 703 through 705, at which point, the intensity from the pig skin is found in block 709. The user finds the absorption ratio of the pig skin and records this value in block 710. Steps 701 through 710 are repeated with all varying degrees of melanin and all emitters and detectors until the max current test for all combinations is tried in block 711. The user again begins with the initial detector and emitter in 701 and runs the average max intensity test, 712 by setting the max intensity in block 713, found during the previous tests. The user presses the max intensity set button 714, which places the microcontroller into capture mode 715 and calculates the current required to achieve this maximum intensity in block 716. The MCU returns the actual intensity the emitter is capable of with the intensity and current parameters given in block 717. At this point, the max intensity is found and is recorded by the user in block 720 before continuing with steps 707 through 710 to find the maximum intensity and pig skin absorption ratios for all detector and emitter combinations. In order to verify that there are no peak or trough anomalies across the current values for each emitter and detector combination, the user performs a manual current test by setting up the initial detector and emitter in 701. The user sets the max current for this emitter in 702 and varies the current of the emitter manually in 718, recording any unexpected peaks or troughs in intensity displayed in block 719. Once the max intensity peak is found during the manual current test in block 720, the process for manual current testing in block 701, 702, and 718-720 are repeated until all emitter and detector combinations are tried. At this point, the user moves to block 721 and reviews the data, in order to pick the best emitter and detector for a method of measuring blood oxygen saturation that reduces the melanin bias in 722. In the example embodiment shown, the best two emitters are chosen for reasons discussed in other figures of this document, and only one detector is chosen. Other example embodiments of the test bench system, use other tests, user interface flows, and procedures, in order to produce the same end result of choosing the best emitters and detector combination for a method of measuring blood oxygen saturation that reduces the melanin bias.

FIG. 8 shows a general usage method of the test bench using, for example, pig skin and an example black-out box. During testing, described previously in the document, in order to prevent ambient light and other light sources to interfere with test results, the following is an example embodiment of usage in which black-out box 801 contains the optical testing portion of the test bench system. 805 represents the detector portion, which is either digital light detector 606 (also 203) or analog photodiode 608 (also 204). 803 represents LED 611. 804 represents pig skin 609 placed on a slide, and as shown, pig skin 804 and the slide is placed between 803 and 805 and held at an even spacing, in order to keep the same distance between the LED and the detector throughout the testing process. 806 represents the cable from detector 805 (also cable 205/402 or cable 206/302), in which cable 806 connects to the test bench board 129/202. Cable 802 (also cable 126 or 127) connects LED 803 to the test bench board 129/202. During the usage, test bench board 129/202 is kept outside the black-out box, 801, in order to give users access to the user interface, as well as to prevent the user interface from causing light interference.

Figure 9:
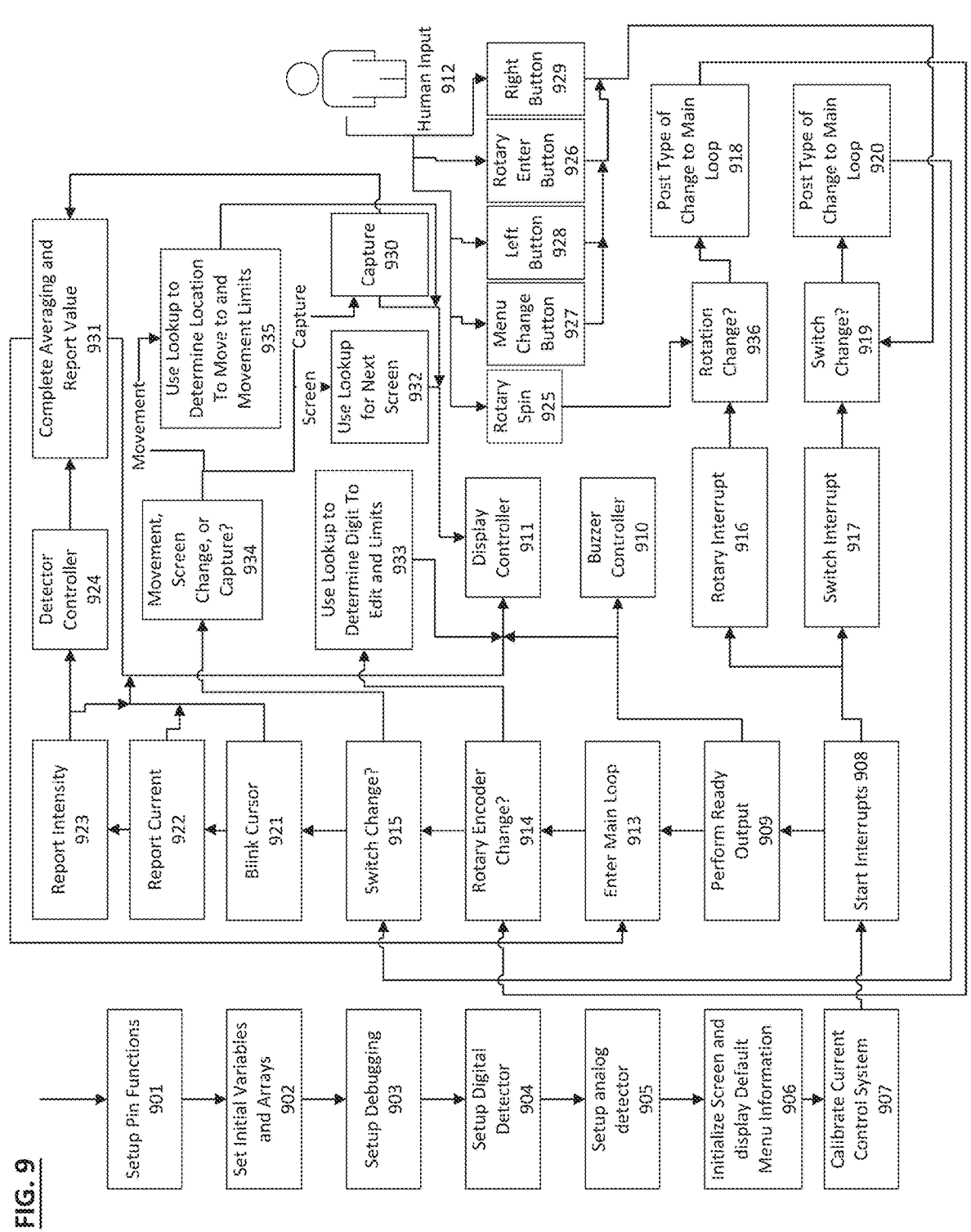
FIG. 9 shows a general software flow, in accordance with the invention, of an example embodiment of a test bench system.

FIG. 9 shows an example of a general software flow of an example embodiment of a test bench system. The program runs on MCU 111 (also 615) and enters at block 901, which sets up all pin functions for the MCU and peripheral hardware. The program sets up the initial values for variables and arrays in block 902 and starts its debugging interface in block 903. The system sets up the digital detector in 904 and the analog detector in 905. The screen is initialized and default menu information posted in block 906. The system calibrates its current control system in block 907 and starts its interrupts in block 908. The interrupts on this system, include, for example, rotary interrupt 916, which senses rotation changes in rotary encoder 106, and switch interrupt 917, which detects switch presses from 104 through 107. The system performs its system ready output in block 909, via display controller 911 and buzzer controller 910, before entering the main loop 913. Main loop 913 begins by checking if a rotary encoder change flag exists in block 914, and checks if a switch change flag exists in 915. The main loop blinks the cursor in 921 before reporting the current in 922 and the intensity in 923. The intensity is reported in 923, via the detector controller 924. Detector controller 924 is used to select which detector the user is currently requesting and sends its intensity data to block 931, where averaging and value reporting are done, before going back to the beginning of the loop 913. Buzzer controller 910 determines the duration of buzzer signaling and when in the program to signal the buzzer. Display controller 911 is responsible for mathematically determining positions on the screen for data output and user input to be displayed, as well as handling the physical parallel interface 624 to the screen 623. If a rotary change flag is detected in 914, look up tables are used to determine the digit to edit and its limits in both directions in block 933 before sending this data to display controller 911. If a switch change flag is detected in 915, the type of change, depending on which button, is determined in 934. The type of changes in 934 are movement, screen change, or capture commands. If a movement command is detected, a look up table is used to determine the location to move to and the movement limits in 935, before sending this data to display controller 911. If a screen change is requested, a look up table is used to determine the next screen to display in 932, before sending this data to display controller 911. If a capture command is requested, the capture begins in 930 as outlined in FIG. 7 before returning data to display controller 911 directly or completing averaging in 931. 921 through 923, as well as 931, all send data to display controller 911 for display on screen 623. The user (human input 912) interacts with the user interface, via rotary spin 925, menu change button 927, left button 928, right button 929, and rotary enter button 926. Rotary spin 925 sets rotary change 936 in rotary interrupt 916 and posts a rotary change 918 to the main loop. Buttons 926 through 929 set a switch change 919 in switch interrupt 917 and posts a switch change 920 to the main loop. The main loop 913 runs until the system is powered off, via the user, reset button 110, or the watch dog software system. Other example embodiments of the test bench software use other methods, block ordering, and flow, in order to produce the same result for detectors and emitters in accordance with the invention.

Pulse Oximeter System

Figure 10:
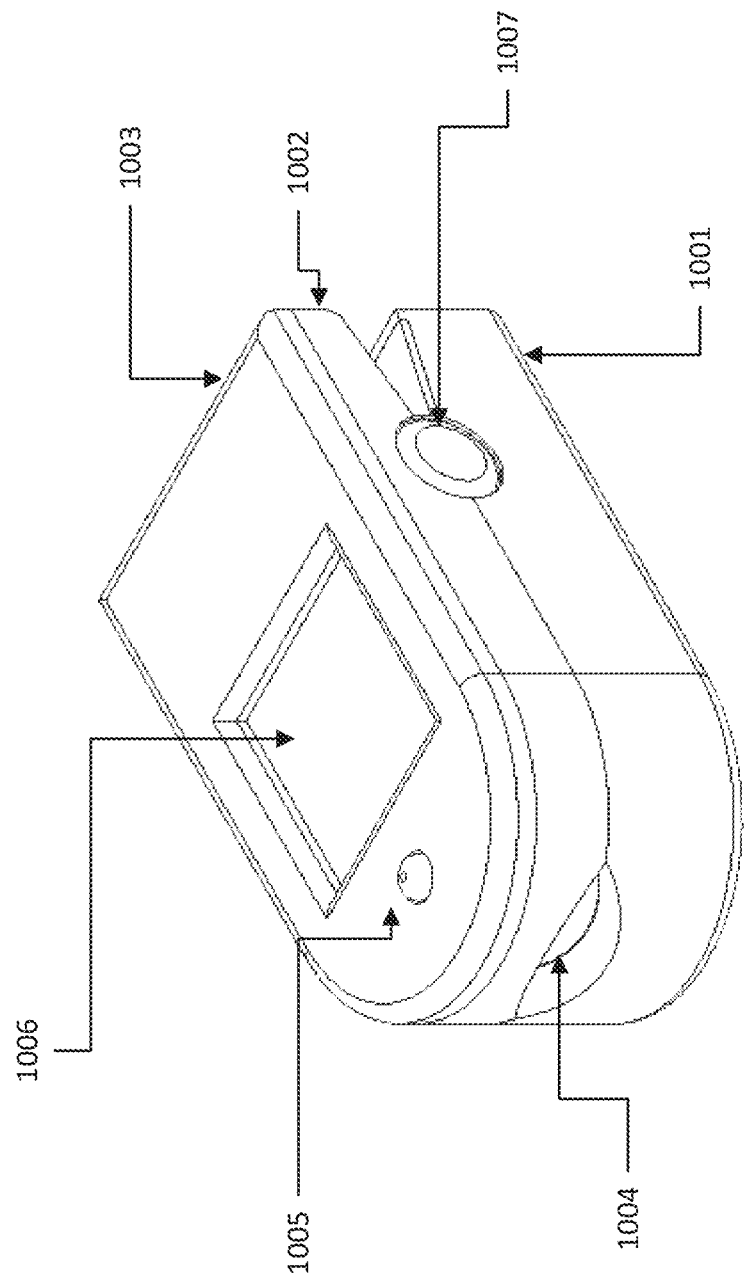
FIG. 10 shows a diagram of an example embodiment of a finger clip design, in accordance with the invention, of a pulse oximeter.

FIG. 10 is a diagram of an example embodiment of a finger clip design of a pulse oximeter. The example embodiment shown in FIG. 10 includes a built-in user interface, including a built-in screen and button. Other example embodiments of the finger clip design, discussed later in this document, do not include a built-in user interface, but rather connect to a patient monitoring system, smart device, or other external user interface. Further, other example embodiments use other input methods for the UI such as, for example, touch screens, capacitive touch, capacitive auto finger detection, and other interface methods. 1001 is the bottom half (or lower half) of the pulse oximeter, further described in FIG. 15. 1002 is the upper half (top half) of the pulse oximeter, further described in FIG. 14, also containing upper lid (top lid) 1003. 1003 is the top lid of the pulse oximeter, which includes the cut-out for the screen portion 1006 of the user interface. 1005 is the user button portion of the user interface, which protrudes from 1003. 1006 includes a clear protective cover attached to 1003, in order to protect the screen. As mentioned above other example embodiments utilize other UI methods and therefore do not contain the cut-out for screen portion 1006 or user button 1005. 1004 is the cut-out in 1001 and 1002, which allows the user finger to be placed in the pulse oximeter. 1007 is the hinge pin that holds 1001 and 1002 together, as well as allows the finger clip to perform in a clamping fashion around the user's finger. The hinge 1007 is designed in such a fashion to allow the lower half, 1001, and the upper half, 1002, to shift to expand finger opening, 1004, to accommodate different sized fingers. The demonstrated embodiment is made out of plastic with rubber inserts, as well as metal springs, wherein the plastic is ABS, PET, and or PLA, and the rubber is primarily TPU. Although the demonstrated example embodiment is made out of primarily plastic with rubber inserts, the meter may take on other forms and shapes using other materials, such as, but not limited to, rubber, foam, vinyl, medical grade materials, antimicrobial materials, and/or metal.

Figure 11:
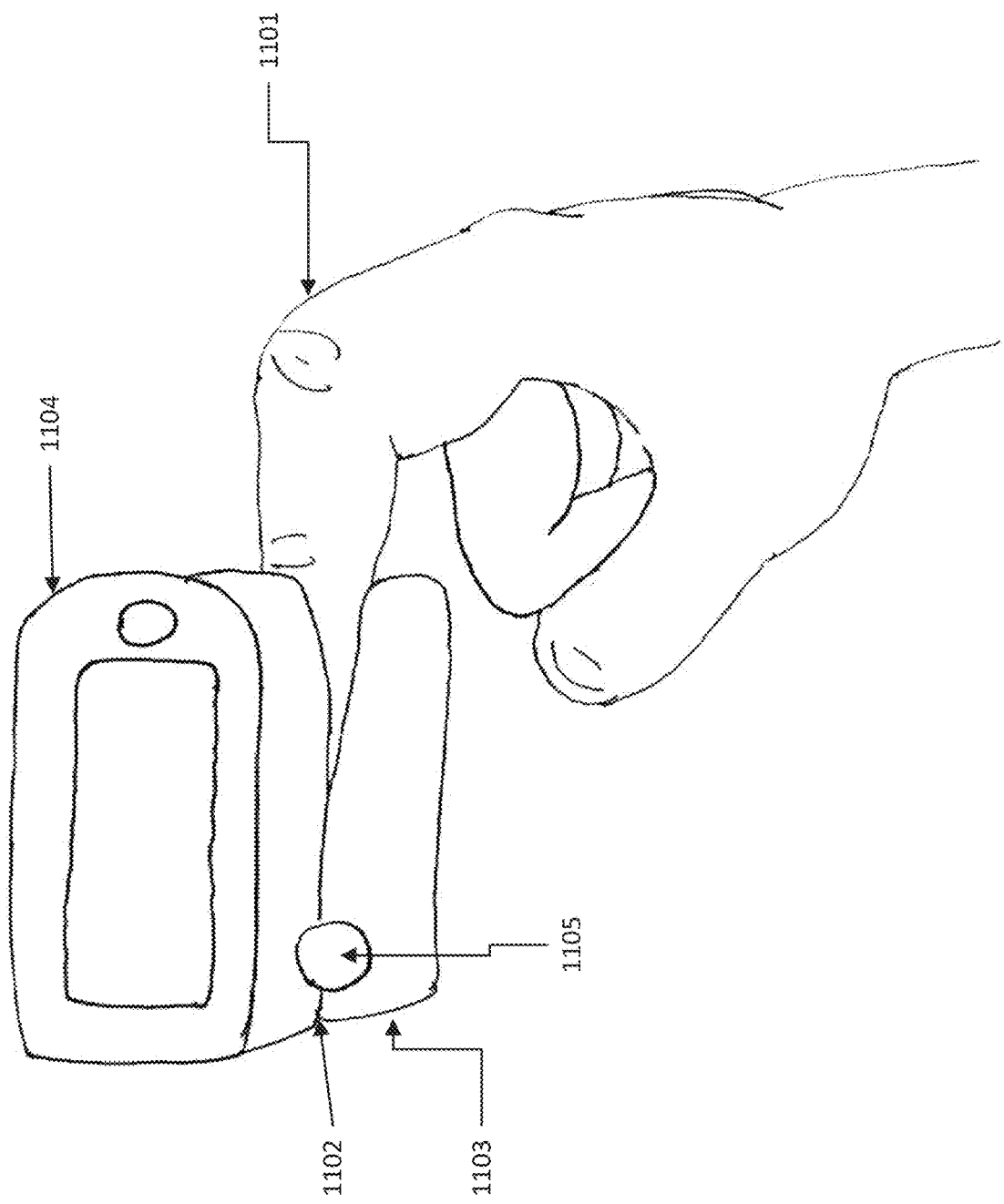
FIG. 11 shows a diagram of an example embodiment of a finger clip design, in accordance with the invention, of a pulse oximeter including an example subject/patient finger placement.

FIG. 11 shows a diagram of an example embodiment of a finger clip design of a pulse oximeter, as previously shown in FIG. 10 with added finger placement. 1101 shows the finger being inserted into finger clamp 1102 between upper portion 1104 (also 1002) and bottom portion 1103 (also 1001). Pivot hinge 1105 (also 1007) is designed to move to allow 1103 and 1104 to dynamically shift, in order to allow finger 1101 to fit snugly between 1103 and 1104 without injuring finger 1101. It is important that finger 1101 fits snugly so that the optics (described later in this document) required for pulse oximetry and contained within 1103 and 1104 are held firmly against finger 1101. The snug fit allows for accurate pulse oximetry calculations, as well as prevents artifacts from finger 1101 movement to interfere with the pulse oximetry reading.

Figure 12:
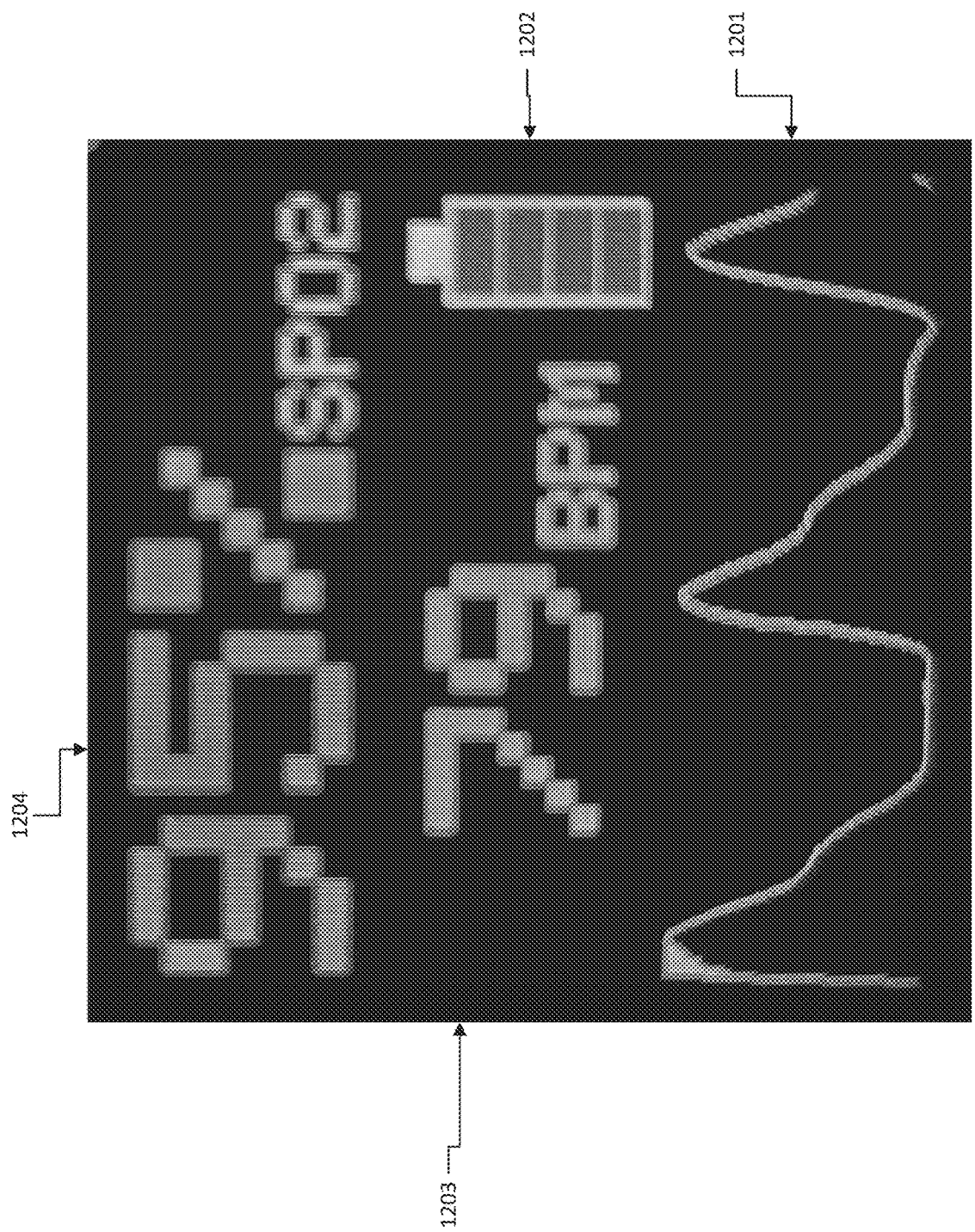
FIG. 12 shows a general layout of an example embodiment of a user interface output for pulse oximetry, in accordance with the invention.

FIG. 12 is an example embodiment of a general lay-out of a user interface for a pulse oximetry system. The user interface described in FIG. 12 is displayed on the screen portion of the user interface. 1201 is the pleth graph, which is used to determine if the meter is getting a good reading, as well as measuring and showing the changes in blood volume, or perfusion changes, in the area that the meter is attached. A good reading is determined by a regular, non-weak signal pleth graph. The pleth graph is also used to determine heart rate based on the peaks of the graph. It is important to note that if the patient's natural heart rate is irregular, the pleth graph will appear irregular as well, even if the meter is getting a good reading. The procedure for pleth graph interpretation is discussed further in the firmware portion of this document. 1202 represents the battery indicator, which is used to determine the amount of remaining battery left in portable meters. One example embodiment uses a segmented meter to demonstrate the amount of remaining battery life, as well as colors to visually indicate good, medium, or critical battery life. 1203 represents the beats/minute of the patient's heart rate. 1204 represents the percentage of blood oxygen saturation (SPO2). 1204 changes color depending on the patient's oxygen level to more easily demonstrate a good (95-100%), moderate (90-95%), or critical (<90%) oxygen level for a layperson. The numbers and text on the screen utilize scalable number, text, and symbol character maps stored in the firmware to accommodate multiple sizes of screens. Other example embodiments of the pulse oximetry system use other styles, arrangements, and data sets to make up the information displayed on their user interface depending on the application required. In systems that are plugged into mains power, it is important that they contain a backup battery, since pulse oximetry blood oxygen saturation levels and heart rate are often considered critical patient care infrastructure. In the case of a wall powered system, 1202 will represent the backup battery level and during mains powered operation, it will display either a charging indicator or a mains power symbol. In other example embodiments, described further in this document, that require full EKG interfaces or full patient monitoring interfaces, such as embodiments that include both pulse oximetry and heart monitoring chest electrodes, the user interface described in FIG. 12 will also include the appropriate required heart rate graphs, ECG, and other monitoring information, such as but not limited to, respiratory rate, BP, temperature, and CO2. Further, other embodiments, for example ring and flexible bracelet embodiments, include additional hardware which requires the UI to display, for example, but not limited to, blood sugar and other blood gas information.

Figure 13A:
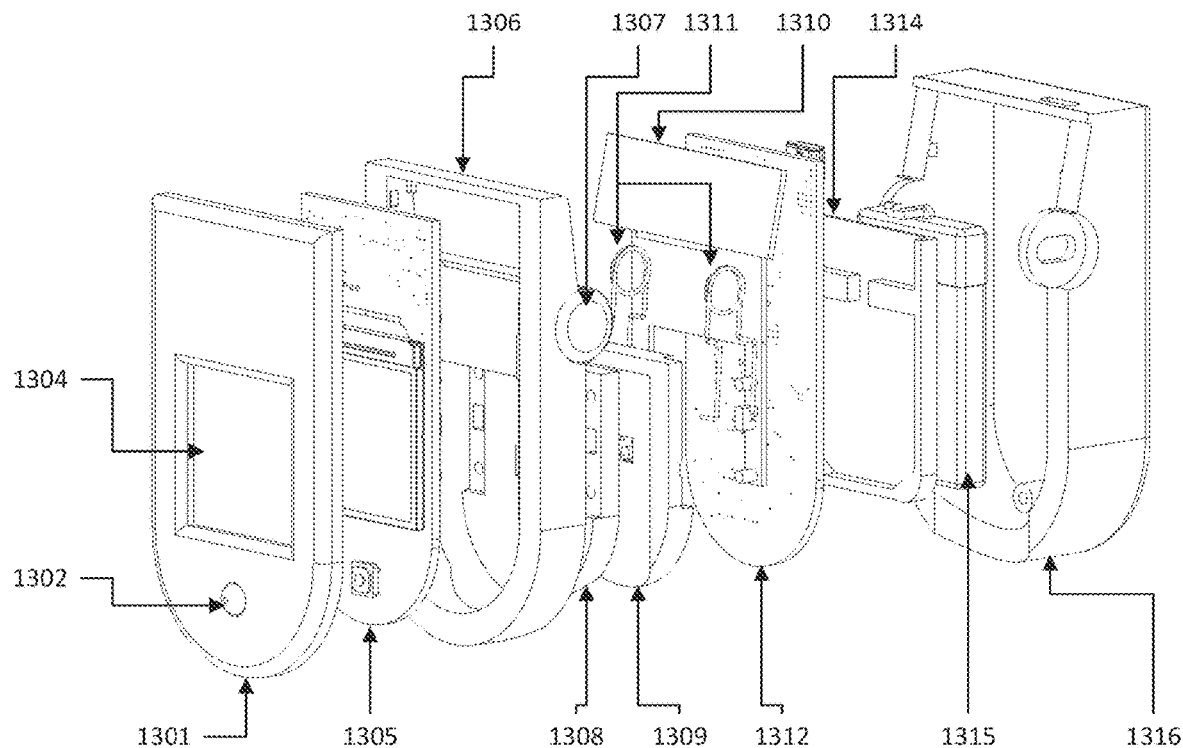
FIG. 13A-13B shows an exploded view of an example embodiment of a finger clip design, in accordance with the invention, of a pulse oximeter.
Figure 13B:
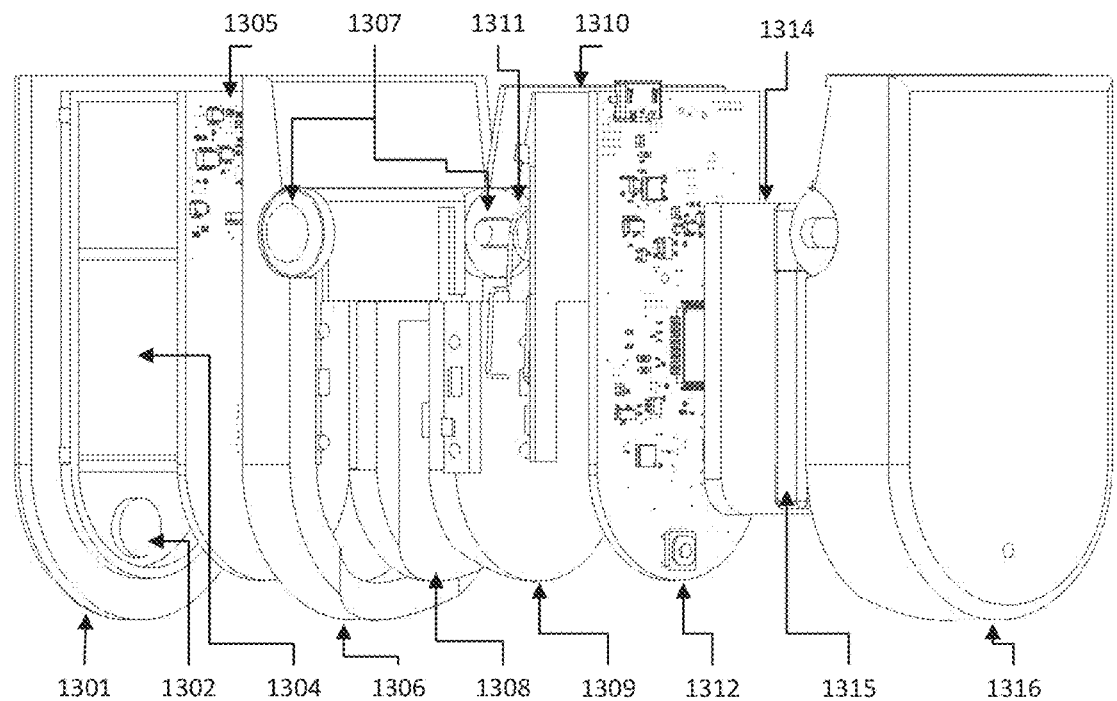

FIGS. 13A and B show an example exploded view of both the front side view (FIG. 13A) and rear side view (FIG. 13B)

of an example embodiment of a finger clip design of a pulse oximeter which reduces the melanin bias. 1301 (also 1003) is the top lid, which contains the cut-out 1304 and protector shield (also 1006) for the screen mounted on the circuit board 1305. 1302 is the user button extension, also part of the top lid 1301, and shown as 1005. Extension 1302 presses the user button, also mounted on circuit board 1305. Upper circuit board 1305, in the example embodiment, is a double layer circuit board, as shown in FIGS. 13A and 13B, where 1305 has different components on both sides. 1306 is the upper case, also shown as 1002. 1306 houses and protects circuit board 1305 and also contains the rubber finger pad 1308, which protects the user's finger from the circuit underneath, as well as gives a comfortable area for the finger to rest. The detector on circuit board 1305 is exposed through a cut-out in 1308 allowing light to pass through the user's finger into the face of the detector. In some example embodiments, 1308 has a clear protector in the cut-out to protect the detector. 1307 (also 1007) are the two hinge pins that connect the upper case 1306 and the lower case 1316 and allow the case to pivot and expand in such a fashion to hold the user's finger. Other example embodiments are designed, for example, with extended sections behind the hinge pins 1307 and/or modified hinge designs to increase the ease of actuating the clip for patients who are elderly and/or others who have problems with hand use and coordination. Further, other example embodiments are designed, for example, with shortened sections behind the hinge pins 1307 and/or modified hinge designs to childproof the design and decrease the ease of actuating the clip for children. 1309 is the lower rubber insert that protects the user's finger from the circuit underneath, as well as giving a comfortable area for the finger to rest, similar to 1308. The LED, or in some embodiments the LEDs (discussed later in this document), on circuit board 1312 is exposed through a cut-out on 1309 allowing light to leave the LED face passing through the user's finger. In some example embodiments, 1309 has a clear protector in the cut-out to protect the LED/LEDs. 1310 is the circuit board protector, which covers the top part of the circuit board 1312 and gives a space for the ribbon cables (not shown in this diagram) to pass, in order to connect circuit boards 1305 and 1312. 1311 are the hinge springs that connect the upper and lower part of the pulse oximeter together and give the pulse oximeter its clamping force to securely attach to a finger. 1312 is the lower circuit board, where in the example embodiment, it is a double layer circuit board shown in FIGS. 13A and B, where it has different components on both sides. 1314 is the battery support cover, which spaces the battery 1315 appropriately below circuit board 1312 to prevent the battery from touching any of the integrated circuits and other components on circuit board 1312. 1315 is the battery, which in the example embodiment shown, is a lithium polymer 3.7V 650 mAh rechargeable battery. Other example embodiments of the pulse oximetry system use other example types of batteries as further described in FIG. 22. 1316 is the lower part of the pulse oximeter case, which houses 1315, 1314, and 1312, and allows 1310, 1311, and 1309 to attach to it. Other example embodiments of 1305 and 1312 use other types of circuit boards, designs, layouts, and components other than those described in the embodiment shown, further described in FIG. 16 and FIG. 17. Other example embodiments use other mechanical arrangements, part orderings, and aesthetic shapes than those shown in FIGS. 13A and 13B. Further, other example embodiments in the pulse oximeter system do not contain the UI components shown in FIGS. 13A and 13B on the pulse oximeter finger clip itself. Instead, in these other example embodiments, these UI components are located in other areas, for example, but not limited to, smart devices, external interfaces, bedside monitoring, and/or patient monitoring systems. Further, other example embodiments use reflective technology where the light from the LEDs enter the human subject/patient and is reflected back to the detector on the same plane as the LEDs. In these example embodiments both the detector and emitter are placed on the same board, which is either 1305 or 1312 in the example shown.

Figure 14:
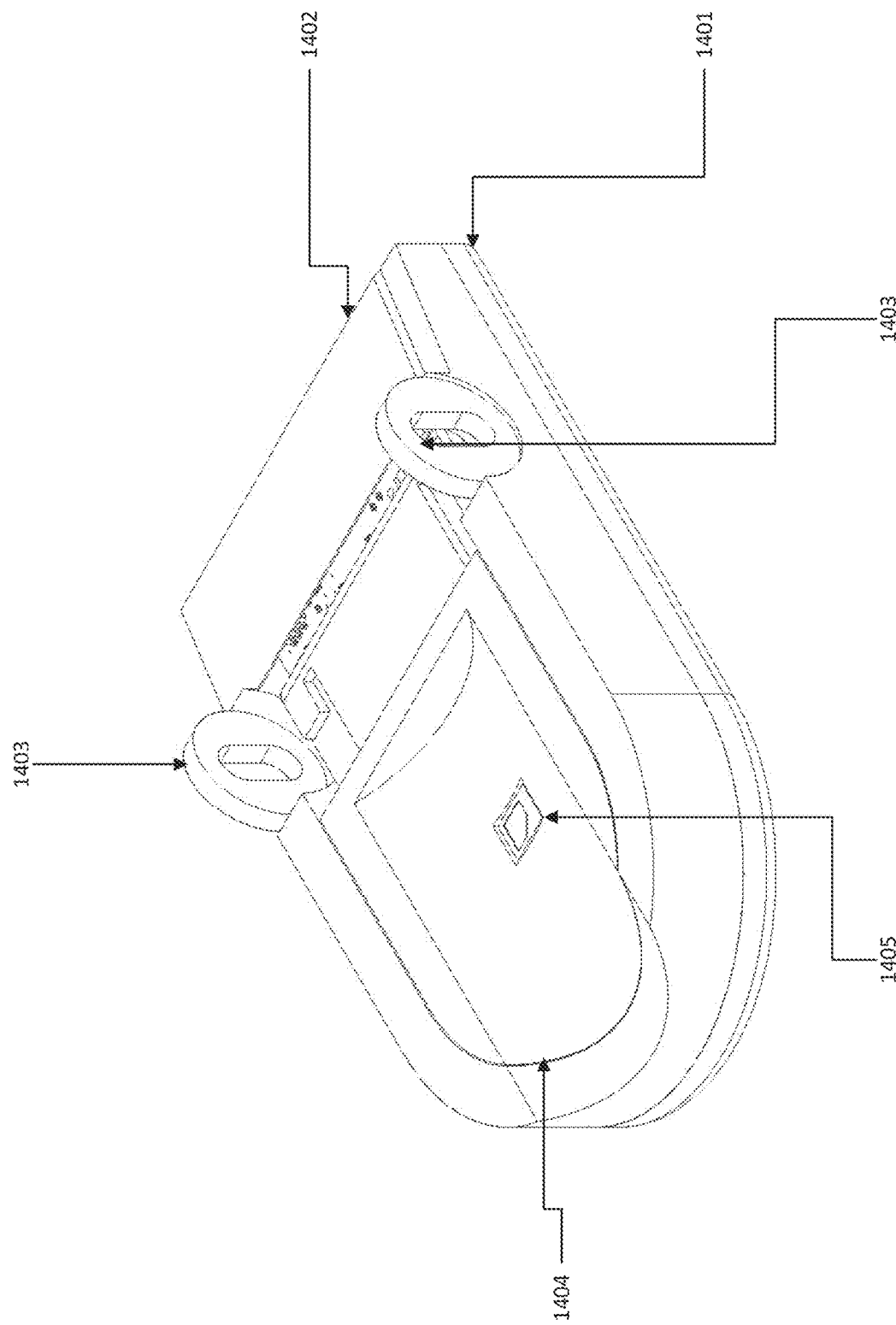
FIG. 14 shows the assembled view of a top half (upper) of an example embodiment of a finger clip design, in accordance with the invention.

FIG. 14 shows an assembled view of an upper (top) half of an example embodiment of a finger clip design of a pulse oximeter, also shown in FIG. 10 and FIG. 13. 1401 is the top lid of the pulse oximeter, also 1003 and 1301. 1402 is the top case of the pulse oximeter, also 1002 and 1306. 1403 is the top half of the hinge that mates with the bottom half of the hinge 1504, and in which hinge pin 1307 (1007) goes through to connect the upper and lower half together. 1404 is the rubber finger protector, also 1308 previously described in FIG. 13, and is made of TPU rubber in the example shown. Other example embodiments use other comfortable materials for 1404, such as, but not limited to, EVA foam, other rubbers, medical grade materials, and/or antimicrobial materials. 1405 is the detector, which goes through 1404 to detect the intensity of the light returned after passing through the subject's/patient's finger. 1405 is mounted to circuit board 1305 and is previously described in FIG. 13. Other example embodiments use reflective methods and use other mounting locations for 1405, as described above.

Figure 15:
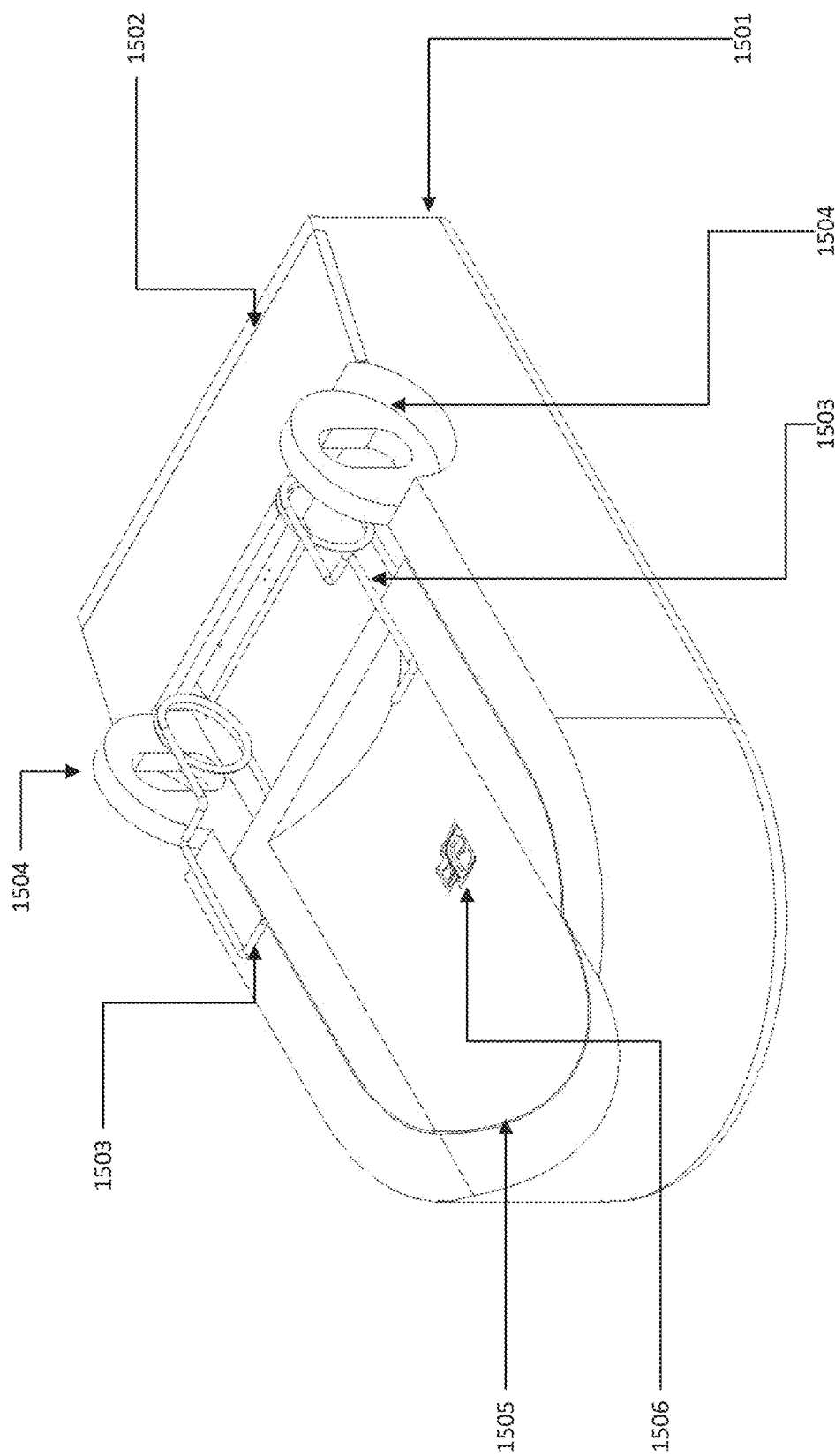
FIG. 15 shows an assembled view of a lower half (bottom) of an example embodiment of a finger clip design, in accordance with the invention.

FIG. 15 shows an assembled view of a lower (bottom) half of an example embodiment of a finger clip design of the pulse oximeter. 1501 is the lower case as described in 1316 and 1001. 1502 is the circuit board protector, also described in 1310. 1503 are the springs, also described in 1311. 1504 is the bottom half of the hinge which mates with 1403, which hinge pin 1307 goes through. 1505 is the rubber finger protector, also described in FIG. 13 as 1309, which protects circuit board 1312. 1506 is the LED/LEDs which goes through 1505 to emit light to pass through the subject's/patient's finger. 1506 is mounted to circuit board 1312 and is previously described in FIG. 13. Other example embodiments use reflective methods and use other mounting locations for 1506, as described above.

Figure 16A:
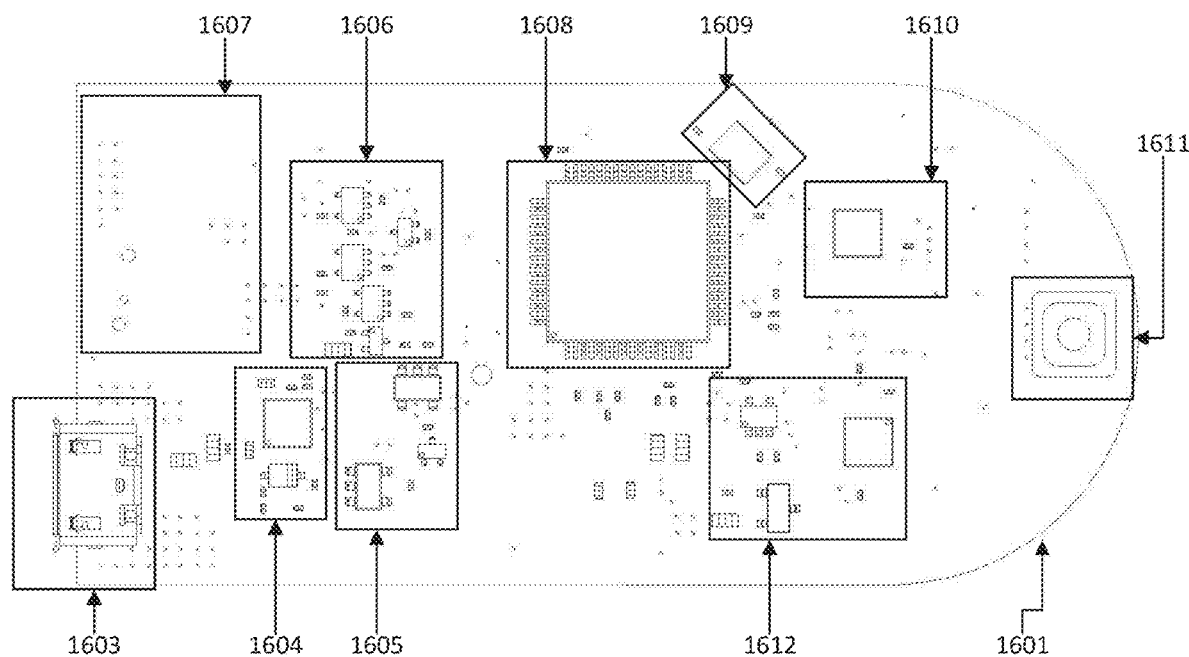
FIG. 16A-16B shows a top and bottom view of an example layout of an example lower (bottom) PCB (printed circuit board) of a pulse oximeter, in accordance with the invention.
Figure 16B:
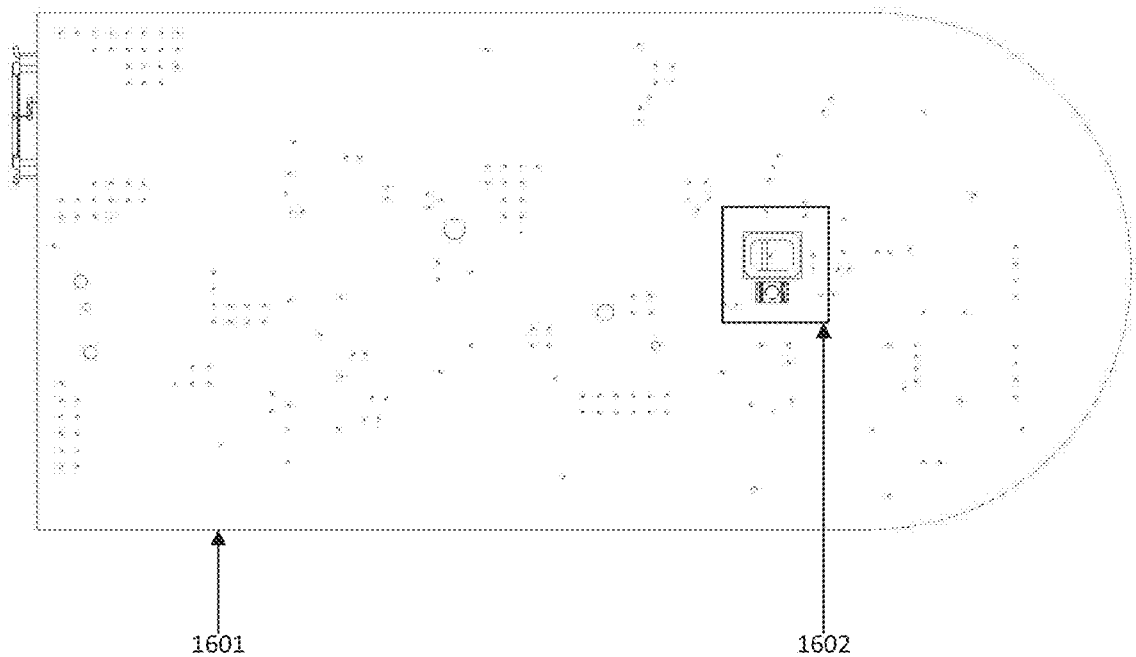
Figure 22:
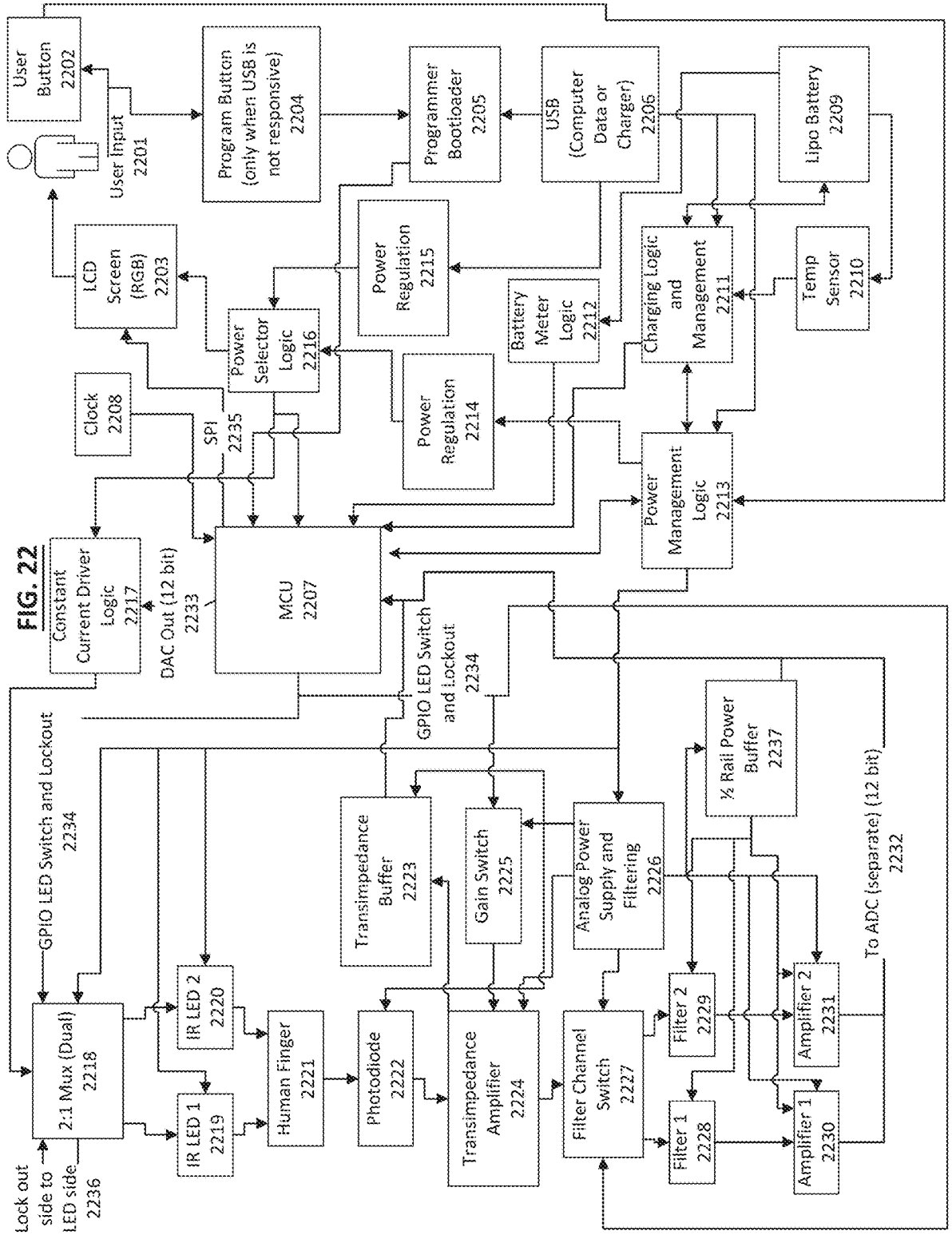
FIG. 22 shows an overview of a general hardware signal flow of an example embodiment of a pulse oximeter system, in accordance with the invention.

FIGS. 16A and 16B show a front and back view of an example embodiment of an example layout of the lower melanin bias reducing pulse oximeter circuit board, also shown as 1312. 1601 is an example embodiment of a PCB which includes the traces and pads for the components. 1602 shows the LED block which contains the LEDs, also 1506, further described in FIG. 22. Other example embodiments use laser light emission methods with the accompanied hardware for 1602. 1603 shows the USB charging connector. In the example embodiment shown, USB connector 1603 is also used as a programming port connected to programmer block 1610. In some example commercial embodiments, the programming feature of 1603 is removed to prevent user access to firmware. In other example embodiments, 1603 is replaced with other charging port styles, such as, but not limited to, barrel jacks, Molex connectors, wireless charging, QI charging, inductive charging, and/or proprietary charging ports. In other example embodiments 1603 is a connector for a patient monitoring system link. 1604 is the charging block, which interfaces between charging port 1603 and battery 1315. In other example embodiments, charging block 1604, as well as charging port 1603, are replaced with a mains power circuit and battery backup controller. Further, in other example embodiments, charging block 1604, as well as charging port 1603, are replaced with a wireless charging method and wireless charging controllers. 1605 is the voltage regulation block, further described in FIG. 22. 1606 is the power management logic block, further described in FIG. 22. 1607 are the contacts which connect this circuit board to upper circuit board 1305 (represented in FIG. 17), via FPC cables (not shown). Other example embodiments use other methods, such as, but not limited to, ZIF connectors, individual wires, and ribbon cables. 1608 is the microcontroller (MCU), and 1609 is the microcontroller's clock source. 1610 is the programmer for microcontroller 1608, and 1611 is the button used to enter programming mode in case of a non-responsive MCU, via 1610. Other example embodiments that do not require on-board programming do not require circuit blocks 1610 and 1611. 1612 is the current source and LED switching block, further described in FIG. 22.

Figure 17A:
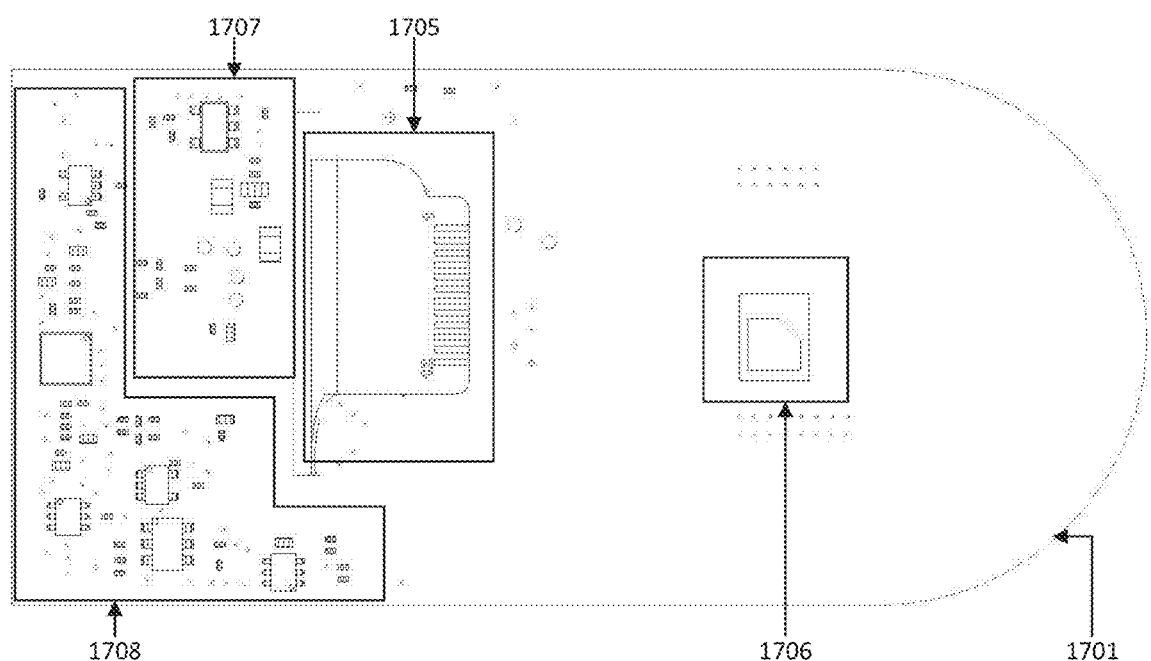
FIG. 17A-17B shows a top and bottom view of an example layout of an example upper (top) PCB (printed circuit board) of a pulse oximeter, in accordance with the invention.
Figure 17B:
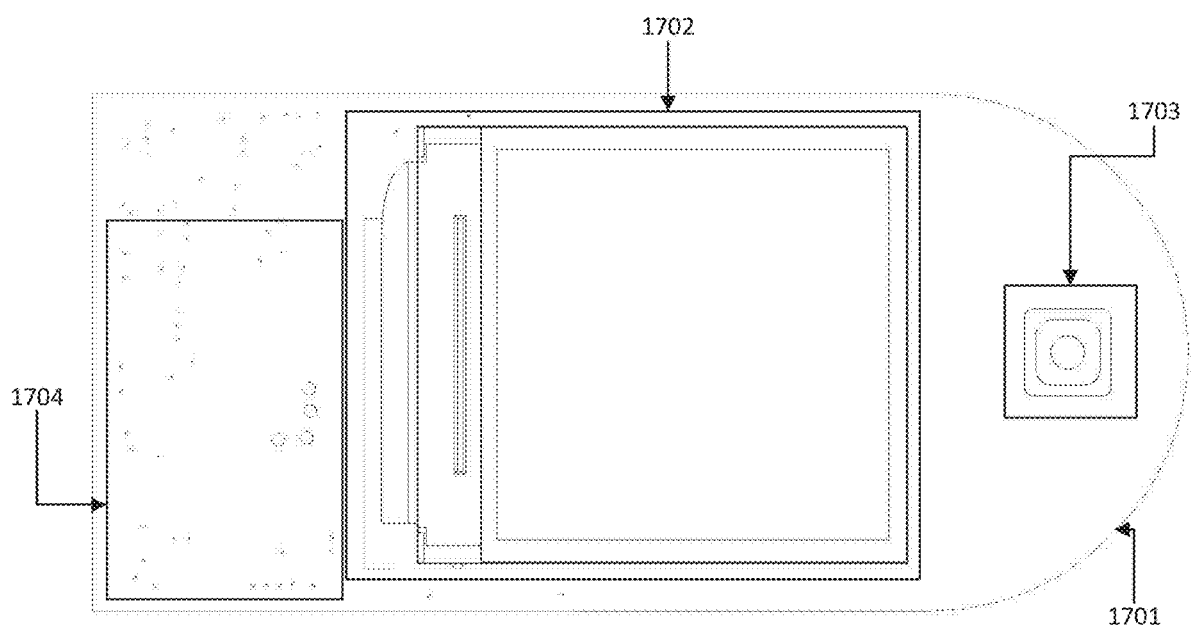

FIGS. 17A and 17B show a front and back view of an example embodiment of an example layout for the upper melanin bias reducing pulse oximeter circuit board, also shown as 1305. 1701 is an example embodiment of a PCB which includes the traces and pads for the components. 1702 is the UI screen, further described in FIG. 22 shown mounted on 1701 visible through 1304, also 1006. 1703 is the user button mounted on 1701 and actuated, via 1302, also 1005. As mentioned above other example embodiments utilize other UI methods and therefore do not contain UI screen 1702 or user button 1703. 1704 are the contacts which connect this circuit board to lower circuit board 1312, via FPC cables (not shown). Other example embodiments use other connecting methods, such as, but not limited to, ZIF connectors, individual wires, and ribbon cables. 1705 is the screen connection block which uses an FPC cable to connect screen 1702 to the other side of board 1701, via a cut-out in board 1701, to allow screen 1702 to mount flush. Other example embodiments use other connection methods for 1705, such as, but not limited to, SMD pins directly under the screen, ZIF, or BGA pins. 1706 shows the detector block which contains the analog photodiode, also 1405, further described in FIG. 22. 1707 is the analog voltage regulation block which powers the analog circuitry in blocks 1706 and 1708 to prevent high frequency noise from the digital circuits from interfering with the pulse oximetry readings. 1708 is the transimpedance amplifier, filtering, amplification, DC offset, and buffering block of the analog circuit. In other example embodiments, blocks 1706-1708 are replaced with other types of detection methods, such as, but not limited to, a photodiode with software filtering and/or a digital detector with software filtering.

Other example embodiments of FIGS. 16 and 17 use other integrated circuits, circuit board shapes, silkscreens, vias, circuit board layouts, and circuit blocks in order to achieve the same effect as the example embodiments explained in FIGS. 16 and 17, in accordance with the invention. The example embodiments shown in FIGS. 16 and 17 show double sided two-layer circuit boards. Other example embodiments of FIGS. 16 and 17 use other circuit layering combinations, such as, but not limited to, single sided, single sided two-layer, single sided multi-layer, and/or double-sided multi-layer.

Figure 21:
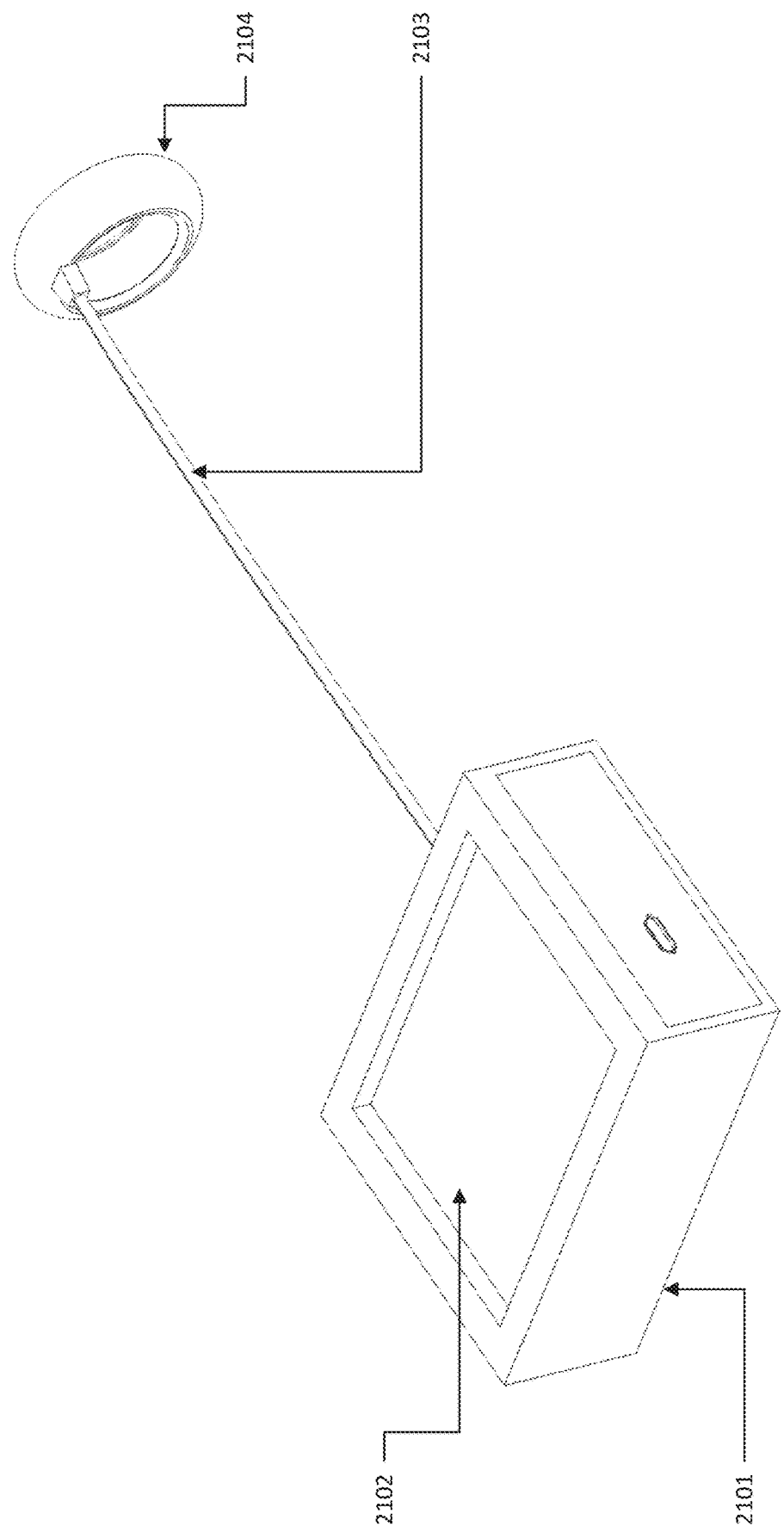
FIG. 21 shows a diagram of an example design of a flexible ring embodiment of a pulse oximeter with an example embodiment of an example wrist mounted UI.

FIG. 18 shows a diagram of an example use of an example embodiment of a ring design of a melanin bias reducing pulse oximeter. 1801 shows the ring containing the melanin bias reducing pulse oximeter, or in some example embodiments only the emitting and detector portions. 1802 is the user/subject/patient finger with ring 1801 on the finger as shown. Ring 1801 is wired, as shown in FIG. 21, or in other example embodiments is wireless connecting to the patient monitoring system or other UI. Other example embodiments of 1801 include, but are not limited to rings with reflective optical technology that go around a patient's arm or leg for patients who are amputees and/or rings used for infant monitoring that are wrist or ankle mounted, as further described as a bracelet or wearable flexible band in FIG. 24. Further, other embodiments of a bracelet or wearable flexible band design are used for patients who are unable to wear traditional pulse oximeters for reasons such as for example, but not limited to, anatomy, age, mental disability, sensitivity issues, and/or ADD.

FIG. 19 shows an example usage of an example embodiment of a ring design of a melanin bias reducing pulse oximeter, including an example wrist mount user interface. 1901 is an example wrist mount interface, also shown as 2101 displaying the information shown in FIG. 12. Other example embodiments use interfaces, such as, but not limited to, interfaces mounted directly on ring 1905, bedside patient monitoring, portable patient monitoring, smart device interfaces, standalone handheld devices, and/or patient monitoring systems. These interfaces are connected to ring 1905, via cable 1904. Other example embodiments use other data transfer methods, such as, but not limited to, existing patient monitoring connections, magnetic contact communication, and/or wireless methods, such as, but not limited to, near field communication, WI-FI, Bluetooth, and/or proprietary communication protocols. 1902 is the arm/wrist that the user interface 1901 is mounted to. 1903 is the user finger, also 1802, that ring 1905 is placed on. Other example embodiments of FIG. 19 use other fingers than the ones shown (1903) for the placement of ring 1905. Further, other example embodiments of FIG. 19 use wrists, arms, or legs as mentioned previously for use in infant, toddler, and amputee monitoring or patients who are unable to wear traditional pulse oximeters for reasons such as for example, but not limited to, anatomy, age, mental disability, sensitivity issues, and/or ADD.

Figure 20:
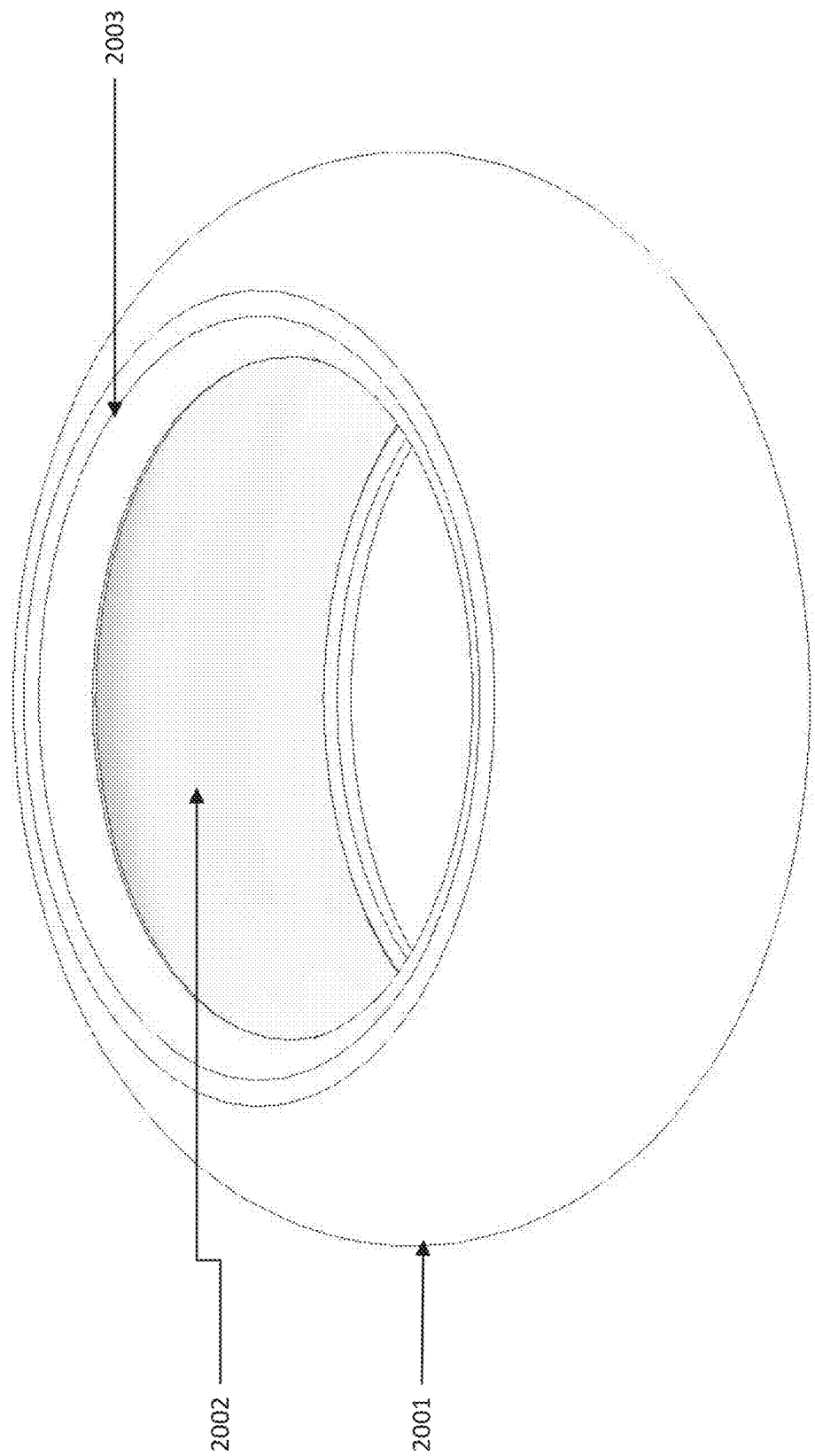
FIG. 20 shows a diagram of an example design of a flexible ring embodiment of a pulse oximeter, in accordance with the invention.

FIG. 20 shows a diagram of an example design of a flexible ring embodiment of a melanin bias reducing pulse oximeter. 2001 is the ring, also 1801, 1905, and 2104, which is made out of flexible rubber (TPU). Other example embodiments of the ring use other materials, such as, but not limited to, elastic, EVA foam, Velcro strapping, medical grade rubbers, foams, and plastics, flexible breathable tegaderm film, and/or other types of flexible rubber or plastic. Other example embodiments of the ring use medical grade material coated, treated, and/or designed with antimicrobial surfaces and/or chemicals. 2002 is the inner chamber of the ring that holds the flexible PCB containing the optics, such as, for example, the emitter and detector mentioned as 1602 and 1706 covered by a protective casing made out of the same material as ring 2001. Other example embodiments use flexible circuit boards containing, for example, a detector and emitter along with necessary filters and emitter control hardware. Further other example embodiments also include the microcontrollers, power sources, and wireless technology. 2003 is the lip that helps hold the flexible circuit board in place, as well as provides a smooth edge for the user's appendage to slip through. An example embodiment of ring 2001, as well as its internal components, is designed to be completely waterproof with some example embodiments, including intrinsic sealing, so that a patient can wear the pulse oximeter continuously, including wet locations such as the shower or bathroom.

FIG. 21 shows an example design of a flexible ring embodiment of a melanin bias reducing pulse oximeter with a wired user interface. Control box 2101 (also 1901) houses the control hardware shown in FIG. 13, including user interface screen 2102, also described in FIG. 12. 2103 is the connecting cable, also described in FIG. 19 as 1904. 2104 shows the ring, also described in FIG. 20, also 1905 and 1801. 2104 and 2101 as shown have a strain relief for cable 2103. As previously discussed, other embodiments of the ring design take on other forms, use other user interfaces, and other communication methods than those shown in FIG. 21. An example embodiment of 2101, as well as its internal components, along with ring 2104 (as described in FIG. 20) is designed to be completely waterproof with some example embodiments including intrinsic sealing.

FIG. 22 shows a broad overview of a general hardware signal flow for an example embodiment of a melanin bias reducing pulse oximeter system and is an example of how components on the circuit boards shown in FIGS. 16 and 17 interact with each other. User 2201 interacts with the hardware, via user button 2202, also 1703, programmer button 2204, also 1611, and LCD screen 2203, also 1702. Button presses from user button 2202 are sent to the power management logic 2213, also 1606, which controls power up, steady state, and power off of the circuit. Program button 2204 communicates with programmer bootloader IC 2205, in order to update firmware on MCU 2207, using data from the USB port 2206 (also 1603). Some example commercial embodiments, which do not require the user to have direct firmware access, do not include the computer data portion of USB port 2206, programmer bootloader 2205, also 1610, programming button 2204, also 1611, and independent power management logic (part of 2213). Program button 2204 is only required to be pressed by user 2201 when the USB part of programmer bootloader 2205 is unresponsive. Independent latching circuitry in power management logic 2213 is required because microcontroller 2207, also 1608, has a delayed boot while waiting for programming bootloader 2205 to release it from program waiting mode 2301. Other example embodiments of the hardware use other programming and firmware update methods than those shown, such as, but not limited to, ICSP, JTAG, SWD, UART, SPI, parallel, and/or wireless update methods, some of which do not require dedicated programmer bootloader IC 2205. MCU 2207 in the example embodiment shown is an NXP Kinetis ARM Cortex M4 running the Teensy Arduino platform with a clock speed of 72 MHz generated by scaling 16 MHz program clock 2208, also 1609. The Kinetis MCU 2207 is chosen for the example embodiment shown due to the on-board 12-bit ADC and DAC, so that the circuit would require minimum external components. Other example embodiments use other MCU ICs instead of the Kinetis MCU 2207, such as, but not limited to, Nordic ICs, other Arduino compatible ICs, and other microcontrollers with suitable peripherals known to those in the field. MCU 2207 runs the software described in FIG. 23, which controls the hardware peripherals and inputs and outputs. DAC output 2233 on MCU 2207 controls the current driver logic 2217 (also part of 1612), which is used to control LED 1(2219) and LED 2(2220), also 1602, through a 2:1 Mux (multiplexer) 2218, also part of 1612. Other example embodiments use other methods to control 2219 and 2220, such as, but not limited to, addressable LEDs, filtered PWM, and/or constant current driver ICs. Mux 2218 uses the second half of the IC to create an LED lock-out through IC loop 2236, controlled along with LED switching, via 2234, via 2207, in order to prevent LED damage during DAC 2233 settling during initial boot. LED 2219 and LED 2220 transmit light through human subject/user/patient finger 2221, also 1101 and 1802, to be received by photodiode 2222, also 1706. In the example embodiment shown, LED 1 2219 is a about 768 nm LED, and LED 2 2220 is a about 960 nm LED. These wavelengths were chosen based on test bench, see FIG. 1, data classifying these LED wavelengths as the combination that has the best transmissive effect in melanin testing for reducing the melanin bias. Other example embodiments use other wavelengths, such as, but not limited to, wavelengths currently on the market, about 640 nm and about 960 nm and/or other IR wavelength combinations. Wavelength combinations currently on the market do not solve the melanin bias issue, but require little additional approval from federal regulators to use with some of the example embodiments, such as, but not limited to, the ring embodiment explained in this document. 2219 and 2220 in the example embodiment shown are separate SMD components. In other example embodiments, in order to save space, both LEDs are combined into a single package. Further, in other example embodiments, instead of LED (2219-2220) light passing through finger 2221 to enter photodiode 2222, the light instead enters finger 2221 and reflects back into photodiode 2222. Light entering photodiode 2222 produces a small current that is converted into a usable voltage using transimpedance amplifier 2224, also part of 1708. Other example embodiments use photodiodes with built in transimpedance amplifiers. Other example embodiments use lasers and other light emission methods instead of LEDs 2219 and 2220, while other example embodiments use phototransistors and other light detection methods instead of photodiode 2222. Furthermore, other example embodiments use digital light detection methods, instead of photodiodes, making the remaining portion of the analog circuit unnecessary as this filtering is done in software. Filter channel switch 2227, controlled by LED switch signal 2234, pipes the intensity voltage data returned from each LED into its own filter, 2228 and 2229, in order to ensure each returned wave form is tracked separately by MCU 2207. Filters 2228 and 2229 are modified off NPX's reference sheet for filter design. The output of filters 2228 and 2229, also part of 1708, are amplified, via 2230 and 2231 before being sent to ADC 2232 on MCU 2207. The analog circuit components are powered, via 2226, also 1707, controlled by power management logic 2213. Transimpedance amplifier 2224 is buffered, via 2223 before having its signal independently sent to MCU 2207, via ADC 2232, for processing. Gain switch 2225 is controlled by MCU 2207, via GPIO LED switch 2234. Gain switch 2225 is responsible for the leveling of the DC waveform components, as well as intensity returns of both LEDs. Half rail power buffer 2237, also part of 1708, is responsible for providing power to the analog filter and amplification stages to simulate a negative reference point, in order to make the waves reproducible by a single supply voltage source. In other example embodiments, the transimpedance output is sent directly to MCU 2207 and software filtering replaces the remaining portions of the analog circuit. Further, in other example embodiments in which digital detector methods are used, software filters are used in a similar fashion. Amplifiers 2230, 2231, and transimpedance amplifier 2224 in example embodiments shown, are based off of high precision op-amps. Other example embodiments use other types of amplifiers, including, but not limited to, other types of op-amps and purpose-built ICs. Power regulation 2214 and 2215, also 1605, are sent through power selector logic 2216, in order to power the digital side of the circuit. 2214 is used when running off of Lipo battery 2209. 2215 is used when running off of USB power 2206, also 1603. Lipo battery 2209 is controlled and charged, via charging logic and management 2211, also 1604. During charging, logic 2211 receives power from USB 2206. Logic 2211 works with temperature sensor 2210, placed on battery 2209, in order to ensure safe and efficient charging. In the example embodiment shown, purpose-built ICs are used for charging logic and management 2211. Other example embodiments use other forms for charging logic and management, such as, but not limited to, MCU driven charging, constant current charging, USB diode controlled charging, and/or removable batteries with external chargers. Lipo battery 2209 is used due to its efficiency and energy density. Other example embodiments use other types of batteries, such as, alkaline, nickel cadmium, lead acid, AGM, gel, lithium ion, lithium phosphate, solid state, sodium composition, ceramic, kinetic, and/or removable rechargeable batteries. Battery meter logic 2212 reports battery usage information to MCU 2207. In the example embodiment shown, 2212 is based off a voltage divider design, however, other example embodiments use other battery meter methods, such as, but not limited to, state of charge ICs, fuel gauge ICs, and/or Coulomb counters. 2235 is the SPI bus on MCU 2207 that interfaces with LCD screen 2203. Other example embodiments use other data communication methods to communicate with their visual outputs, such as, but not limited to, $I^2C$, 1-wire, UART, and parallel. LCD screen 2203 in the example embodiment shown is an RGB LCD screen. An RGB screen is used, in order to use colors to represent different oxygen level ranges to increase clear interpretation and ease of use for a layperson. Other example embodiments that do not require this enhanced feature may use monochrome screens, such as, but not limited to, E-ink, single color OLED, LED arrays, and gray scale LCDs. Further, other example embodiments use other dimensions and configurations of screens, as well as other types of screens, such as, but not limited to, OLED, smart device interfaces, and/or computer interfaces. Other example embodiments that require wireless technology use, for example, external wireless transceivers and transceiver ICs with data streams connected to MCU 2207, while other example embodiments use other wireless technologies, such as, for example, SoCs. FIG. 22 represents an exemplary method of connecting components and their signal paths, and those experienced in the field will recognize that there are other methods, signal paths, and ICs to produce the same result in accordance with the invention. Other example embodiments have audio and/or voice synthesizers as part of their UI to give an auditory message regarding the readings displayed on screen to increase ease of use and make the device visual impairment friendly. Further, other embodiments, for example ring and flexible bracelet embodiments, include additional hardware not shown in FIG. 22, which includes for example, but not limited to, ECG, temperature, $CO_2$, blood sugar and other blood gas information sensors.

Figure 23:
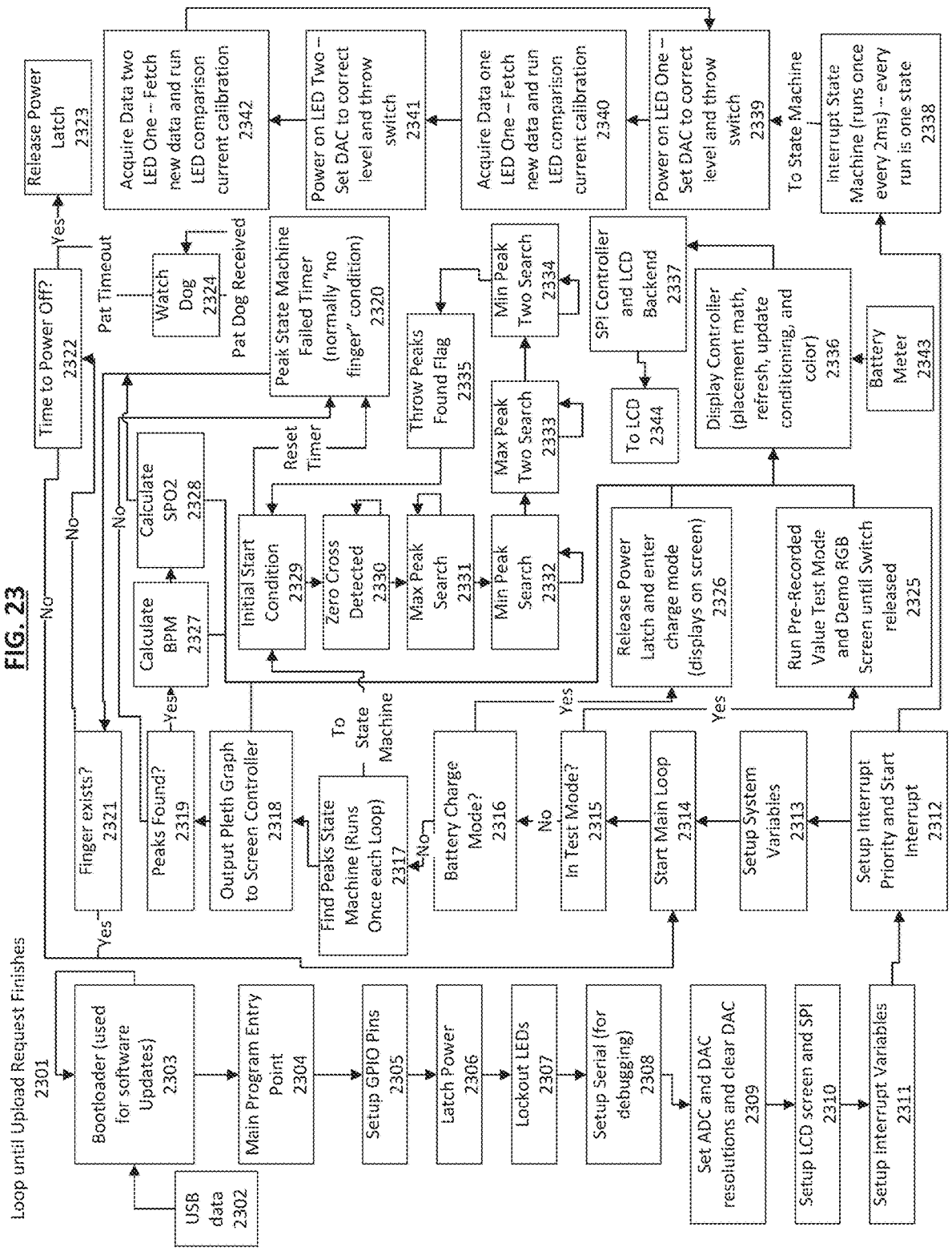
FIG. 23 shows an overview of a general software signal flow of an example embodiment of a pulse oximeter system, in accordance with the invention.

FIG. 23 shows a general overview of a software signal flow that runs, for example, on MCU 2207 of one example embodiment of a melanin bias reducing pulse oximeter system. The entry point of the program starts at 2301, which loops until the pending upload request 2301 from USB data 2302 finishes, or until bootloader 2303 releases the software update stage. 2301 and 2203 are controlled by the bootloader IC 2205. Other example embodiments use other data streams for program data other than USB data 2302, such as, but not limited to, ICSP, JTAG, SWD, UART, SPI, and/or wireless update methods. Further, other example embodiments that do not give the user direct access to perform firmware/software updates, do not require blocks 2301-2303, and these embodiments start at block 2304. Once bootloader 2303 exits, main program entry point 2304 is entered. Main program entry point 2304 begins the set-up process, which includes setting up GPIO pins 2305, latching power control 2306, LED lock out 2307, setting up serial debugging 2308 (not performed in many commercially released embodiments), setting ADC and DAC resolutions, as well as clearing DAC data 2309, and setting up LCD screen and SPI bus 2310. This set up continues by setting up interrupt variables 2311, setting up interrupt priority, and starting interrupt 2312, which has a starting entry point of 2338, setting up system variable 2313, and entering main loop 2314. Further, other example embodiments use another order for initial setup steps, in order to produce the same resultant effect, in accordance with the invention. Main loop 2314 is a loop in which the program runs all remaining functions from and only temporarily exits to run interrupts, or permanently exits when the release of power latch block 2323 runs at program exit. Main loop 2314 first checks if the system is in test mode 2315, which is used for verifying that all components are functioning, as well as demonstrating the user interface. If the system is in test mode, block 2325 runs, which outputs a pre-recorded set of intensity values to the BPM and SPO2 control blocks, which outputs their information to the display controller 2336. If the system is not in test mode, the system checks if battery charge mode 2316 should be entered. If so, charge mode 2326 is entered and the power latch is released, so that the system will automatically power off when the charging source is removed. Charge mode 2326 displays the charging icons on the screen, via the display controller 2336. If the system should not enter charging mode, the peak state machine runs, 2317. The state machine runs once per loop. The state machine has the following states, which are used during the peak found block, 2319. The states are, initial condition 2329, zero cross detection 2330, which loops until zero cross is found, max peak search 2331, which runs until a maximum peak is found, min peak search 2332, which runs until a min peak is found, max peak 2 search 2333, which runs until the second max peak is found, and min peak 2 search 2334, which runs until the second minimum peak is found. By finding two min and max peaks, the system is able to calculate beats per minute in the BPM calculation block 2327 by calculating the time between peaks. Once all peaks are found, the peaks found flag is thrown in 2335, which is used by 2319. During the initial start process 2329, the timer for detecting if the state machine failed in block 2320 is reset. A state machine failure, being triggered from timer 2320, normally occurs if the user's/subject's/patient's finger is removed from the pulse oximeter, which is checked in block 2321. If a finger still exists in block 2321, the main loop starts over in 2314. If the finger does not exist in block 2321, the timer for power off in 2322 is checked. If it is not time to power off, again the loop starts over in 2314, otherwise, the power latch is released in 2323, and the program exits when the device shuts off. After the state machine runs in 2317, the pleth graph is generated and output to the screen controller 2336 in 2318. The pleth graph is generated by taking raw intensity data and using a maximization algorithm to dynamically stretch the data to appropriately fit the screen without distorting it. After outputting the pleth graph, it is checked whether peaks have been found in 2319. If no peaks are found, the peak state machine failed timer is queried in 2320, otherwise, BPM is calculated in 2327 and $SPO_2$ is calculated in 2328, both of which output their data to display controller 2336, before verifying if the finger still exists in 2321. Battery meter 2343 also outputs its data to display controller 2336 as new battery states are delivered. Display controller 2336 is responsible for refresh commands, update conditioning to ensure reduced flickering during updates, color management, text scaling, and screen placement math, in order to create a bitmap, which is sent to SPI controller software and LCD back-end software 2337. 2337 is responsible for sending appropriate SPI commands and data streams to control LCD 2344, also 2203. Watch dog timer 2324 runs in the background and is "patted" during each iteration of the loop. If the watch dog timer 2324 has a "pat" time-out, in which the loop has failed to "pat" the watch dog before the timer runs out, it will force a release of the power latch 2323 to shut off the device and end any hung software. Interrupt entry point 2338 is the starting point for the interrupt 2312, which runs once every 2 ms and temporarily halts the main loop while it runs. The interrupt function itself is a state machine where every state is one run of the interrupt. Other example embodiments use other interrupt run times depending on processor load and required capture times. Further, other example embodiments use a multi-core MCU to independently run the state machine and other functions on separate cores/threads. The first state of the interrupt state machine 2339, which powers on the first LED (2219) by setting the correct DAC level (2233) and throwing the switch (also Mux 2218). The second state 2340 acquires data from the first LED (2219) by running LED comparison calibrations used to level both LED DC offsets and then fetching and recording the data. The LED controller (also Mux 2218) is also put into lock-out mode at the end of this state, in order to prevent damage to the LED during the following state. The next state 2341 powers on the next LED (2220) by setting the correct DAC level (2233) and throwing the switch (also Mux 2218). The final state 2342 acquires data from the second LED (2220) by running LED comparison calibrations used to level both LED DC offsets and then fetching and recording the data. The LED controller (also Mux 2218) is also put into lock-out mode at the end of this state in order to prevent damage to the LED during the following state. The state machine repeats and goes back to state 2339 on the next interrupt iteration. Other example embodiments that require wireless transmission have wireless transmission blocks connected to the display controller 2336, and/or send pre-display controller data structures wirelessly for display on the UI device. Further, other example embodiments use other software designs, block ordering, state machines, and software signal flows, in order to produce the same resultant effect, in accordance with the invention. Example embodiments that use wireless transmissions have wireless control blocks in other locations in the software flow.

Figure 24:
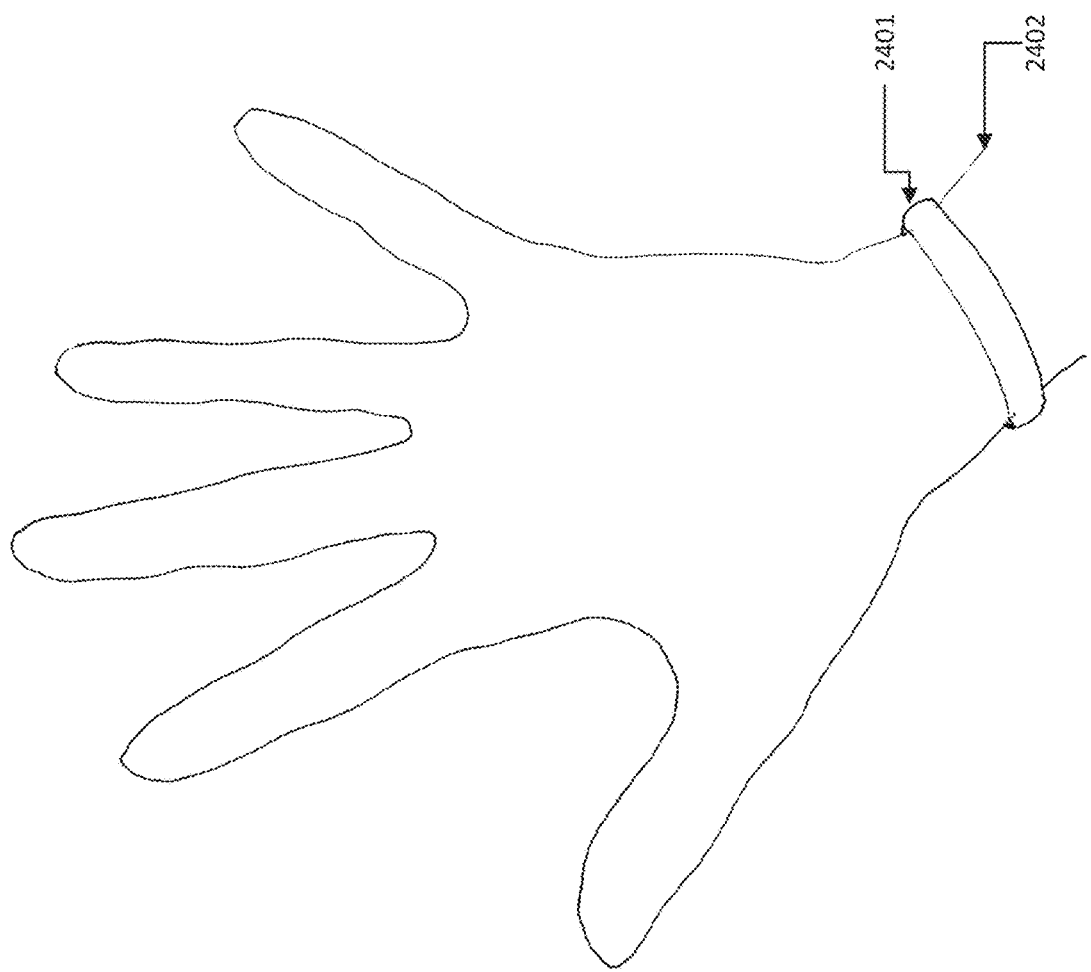
FIG. 24 shows a diagram of an example embodiment of a bracelet or wearable flexible band design, in accordance with the invention, of a pulse oximeter.

FIG. 24 shows a diagram of an example use of an example embodiment of a bracelet design or wearable flexible band of a melanin bias reducing pulse oximeter, similar to the ring shown in FIG. 18. 2402 shows the bracelet containing the pulse oximeter, or in other example embodiments only the emitting and detector portions. 2401 is the user/subject/patient arm or wrist, with the bracelet 2402, placed on it as shown. Bracelet 2402 is wired in a similar method to the ring embodiment, as shown in FIG. 21, or is wireless connected to the patient monitoring system or other UI as previously described. Other example embodiments of 2402 include, but are not limited to, bracelets with reflective optical technology that go around a patient's arm or leg for patients who are amputees and/or bracelets used for infant and toddler monitoring that are ankle/wrist worn. Further, other embodiments of a bracelet or wearable flexible band design are used for patients who are unable to wear traditional pulse oximeters for reasons such as for example, but not limited to, anatomy, age, mental disability, sensitivity issues, and/or ADD. Bracelet 2402 is designed utilizing similar materials and similar fashion, as described in FIG. 20 for the ring embodiment. This design allows for flexibility in the size of the appendage the bracelet is placed on.

Figure 25:
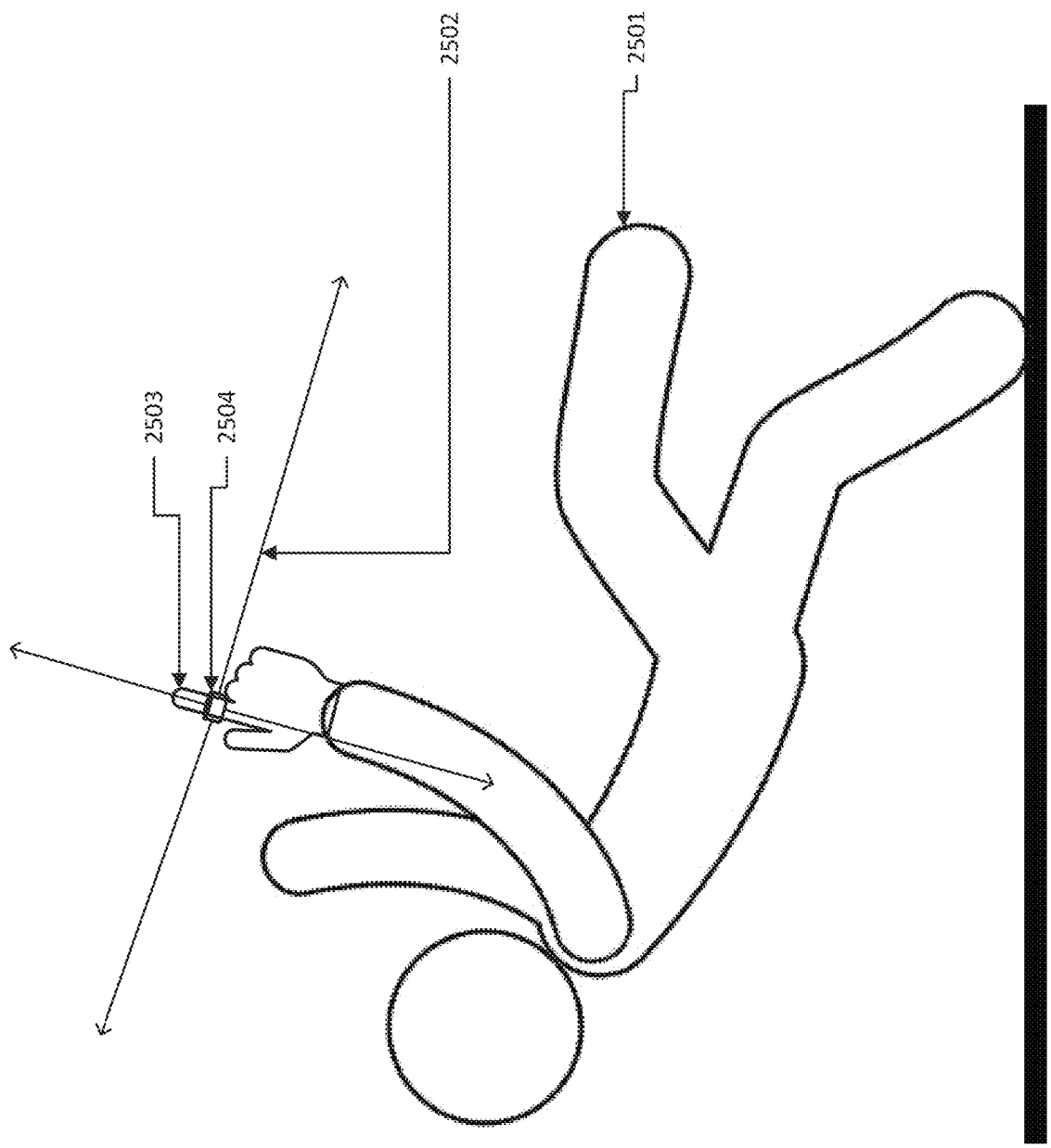
FIG. 25 shows an example fall detection and bed alarm monitor usage, in accordance with the invention, of an example ring embodiment of a pulse oximeter.

FIG. 25 is a diagram showing fall detection and bed alarm integration for a melanin bias reducing pulse oximeter system. 2501 demonstrates a user in the process of falling. 2502 shows examples of the force vectors being registered by the pulse oximeter, indicating that user 2501 is falling. 2503 represents the appendage the pulse oximeter is placed on. 2504 represents the pulse oximeter on the appendage. All embodiments of the pulse oximeter system are capable of implementing this feature utilizing additional hardware in FIG. 22, such as, for example, but not limited to, a gyro sensor for measuring angular rate, accelerometers for measuring acceleration and velocity, altitude sensors for measuring height, angular velocity sensors for measuring angular velocity (some manufacturers consider these gyro sensors or gyroscopes), magnetometers for measuring magnetic field and providing a digital compass, and/or single or multi axis inertia sensors often referred to as an IMU or inertial measurement unit. Further, other embodiments implement a sensor fusion algorithm which combines the data from multiple sensors previously mentioned to provide more accurate sets of measurement data. The ring and bracelet embodiments are the most practical and useful embodiments when used in a wireless system to include this fall detection and bed alarm capability. An example usage of this technology is in hospital and nursing home settings for total patient monitoring that is comfortable for the patient and easy to implement. The technology described in FIG. 25 is also used in other example embodiments for comfortable and easy multi-location bed, chair, and bathroom exit/standing alarms functioning similarly to the current more cumbersome bed and chair alarm systems.

Figure 26:
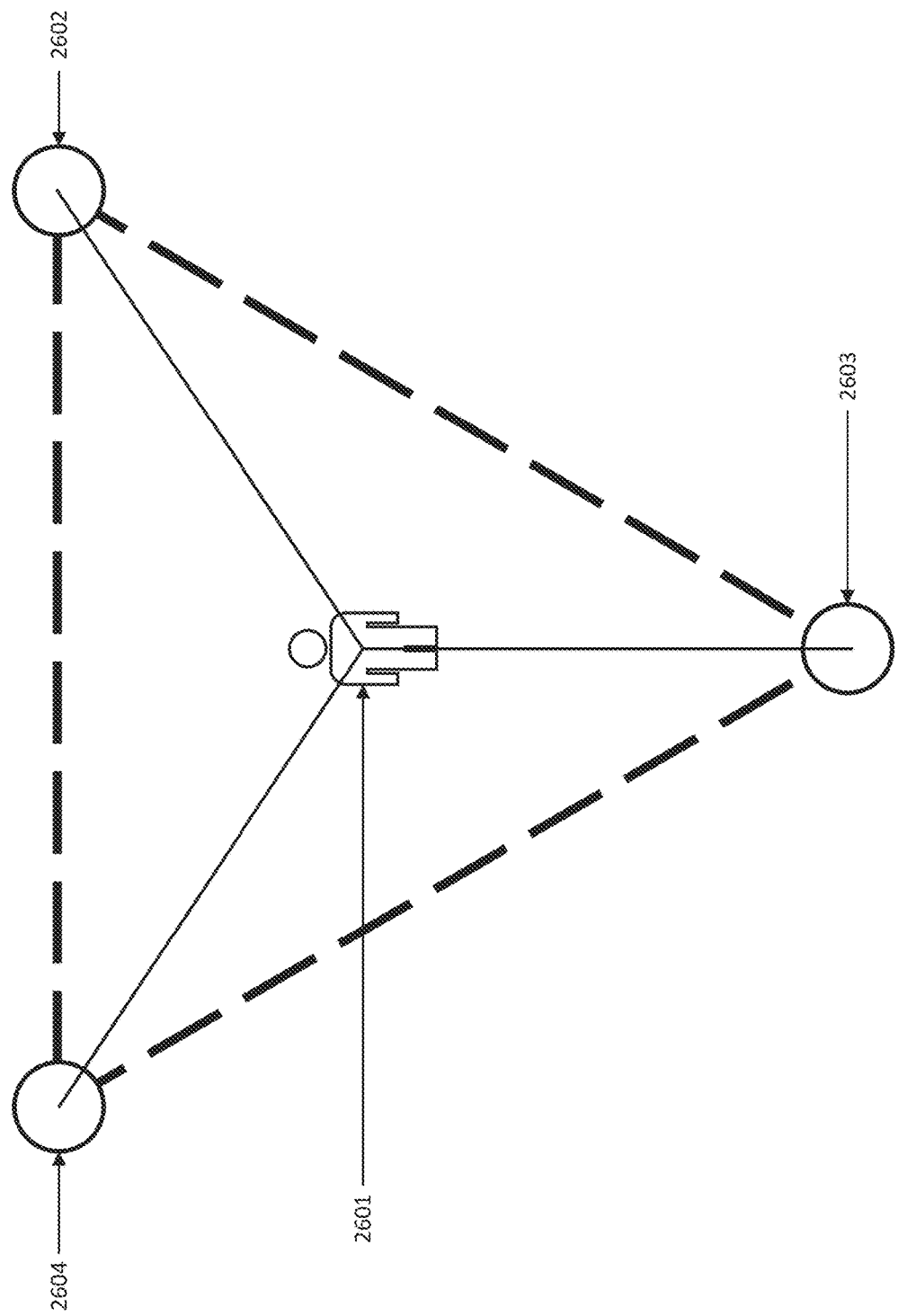
FIG. 26 shows an example of a patient location tracking triangulation method, in accordance with the invention, of an example ring embodiment of a pulse oximeter.

FIG. 26 shows a diagram of an example location detection method for the melanin bias reducing pulse oximeter system. All embodiments of the pulse oximeter system are capable of implementing this feature utilizing additional hardware in FIG. 22, such as, for example, but not limited to, GPS, Wi-Fi triangulation, cell tower triangulation, mesh networks, RFID/NFC, or similar type door and hallway monitor sensors, and/or proprietary radio system triangulation. The ring and bracelet embodiments are the most practical and useful embodiments when used in a wireless system to include this location detection capability. An example usage of this technology is in hospital and nursing home settings for total patient monitoring that is comfortable for the patient and easy to implement. 2601 represents the location of the user, and 2602-2604 represents the communication stations in which the triangulation is performed. Other example embodiments, use for example, but not limited to, GPS links to perform the tracking function and therefore do not require radio triangulation on the same plane as the user/subject/patient as shown in FIG. 26. Further, other example embodiments use this technology as a tracking device to assist family members in geo-fencing as well as retrieving location information for children, adults with disabilities, and the elderly while also providing monitoring of vitals in the same device.

Heart Telemetry System

Figure 27:
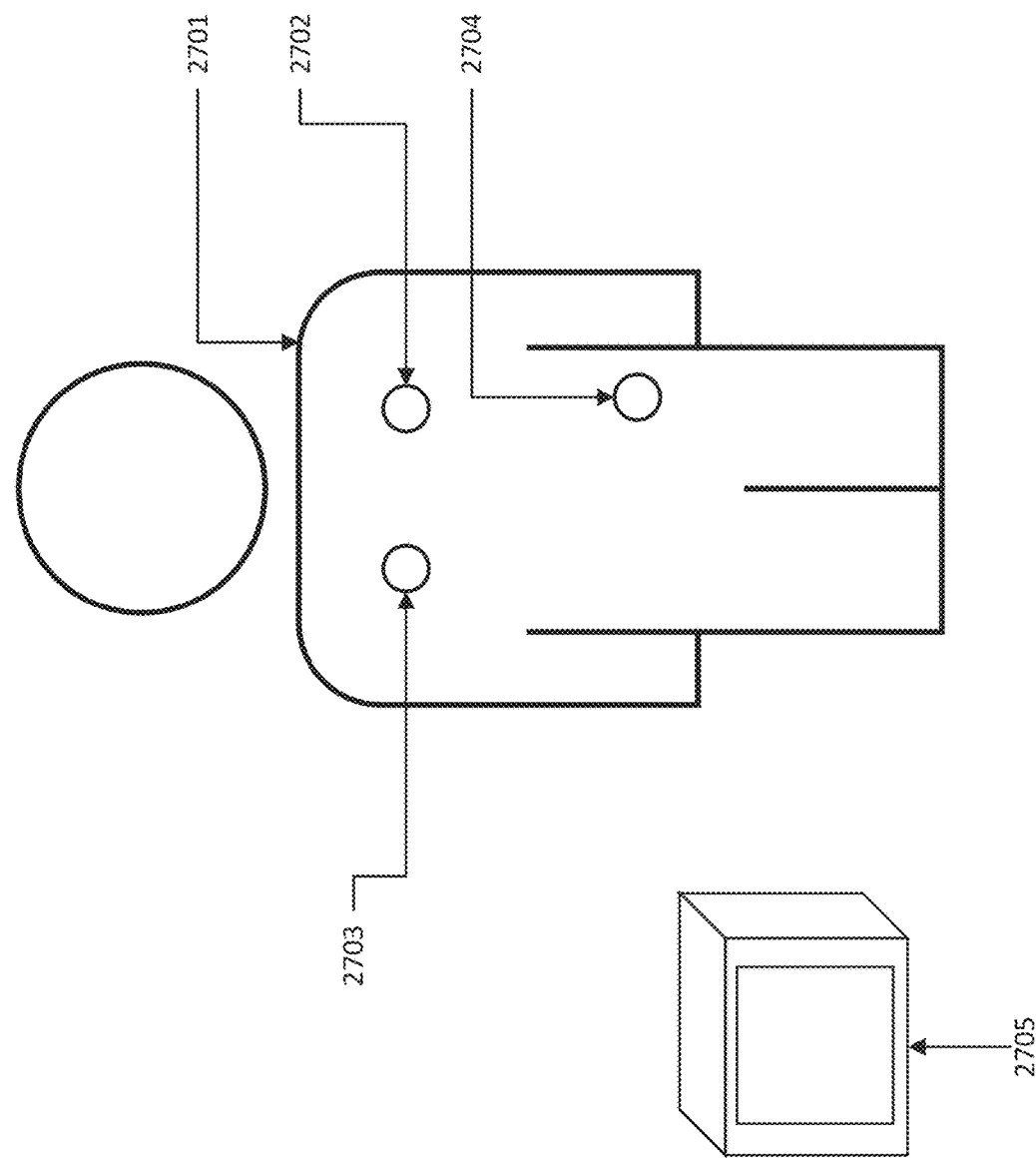
FIG. 27 shows an example embodiment of a completely wireless heart telemetry monitoring system with an example embodiment of wireless patient/subject worn conductive pads, in accordance with the invention.

FIG. 27 shows an example embodiment of a completely wireless heart telemetry system. User 2701 wears heart monitor pads 2702-2704, which wirelessly sends data to patient monitoring system 2705. The example locations of monitoring pads 2702-2704 are meant for demonstration purposes and are not to be considered the only locations or quantity of pads required for heart telemetry monitoring. In the example shown, 2702-2704 utilize disposable snap on or clip on pads similar to those used in current heart telemetry systems, which are in contact with the patient skin. Snapped or clipped onto these pads are the reusable devices, which include the hardware required to wirelessly transmit the heart telemetry data to the patient monitoring system 2705. This hardware includes for example, but is not limited to, filtering, MCU, wireless SoC, battery, and isolation technology. The signals from 2702-2704 must be synchronized, in order for the system to work properly using, for example, time of flight calculations and/or synchronized time stamping. One example embodiment of the system, described in FIG. 27, utilizes independent grounds for 2702-2704, while other example embodiments use an interconnected and centralized ground. One example embodiment of FIG. 27 utilizes Bluetooth as its wireless communication method, while other example embodiments use other wireless communications, such as, but not limited to, Wi-Fi, LoRa, or other proprietary wireless communications methods. 2705, in the example embodiment shown in FIG. 27, is a bedside patient monitoring system. Other example embodiments use bedside systems connected to hospital wide patient monitoring systems, pocket patient monitoring systems connected to bedside and/or hospital wide patient monitoring systems, independent pocket patient monitoring systems, smart device patient monitoring systems, portable patient monitoring systems, or hospital wide patient monitoring systems, instead of bedside patient monitoring system 2705. The portion of the system worn on the user 2701 in FIG. 27 is designed to be completely waterproof for continuous patient monitoring, including damp locations, such as the bath or shower.

Figure 28:
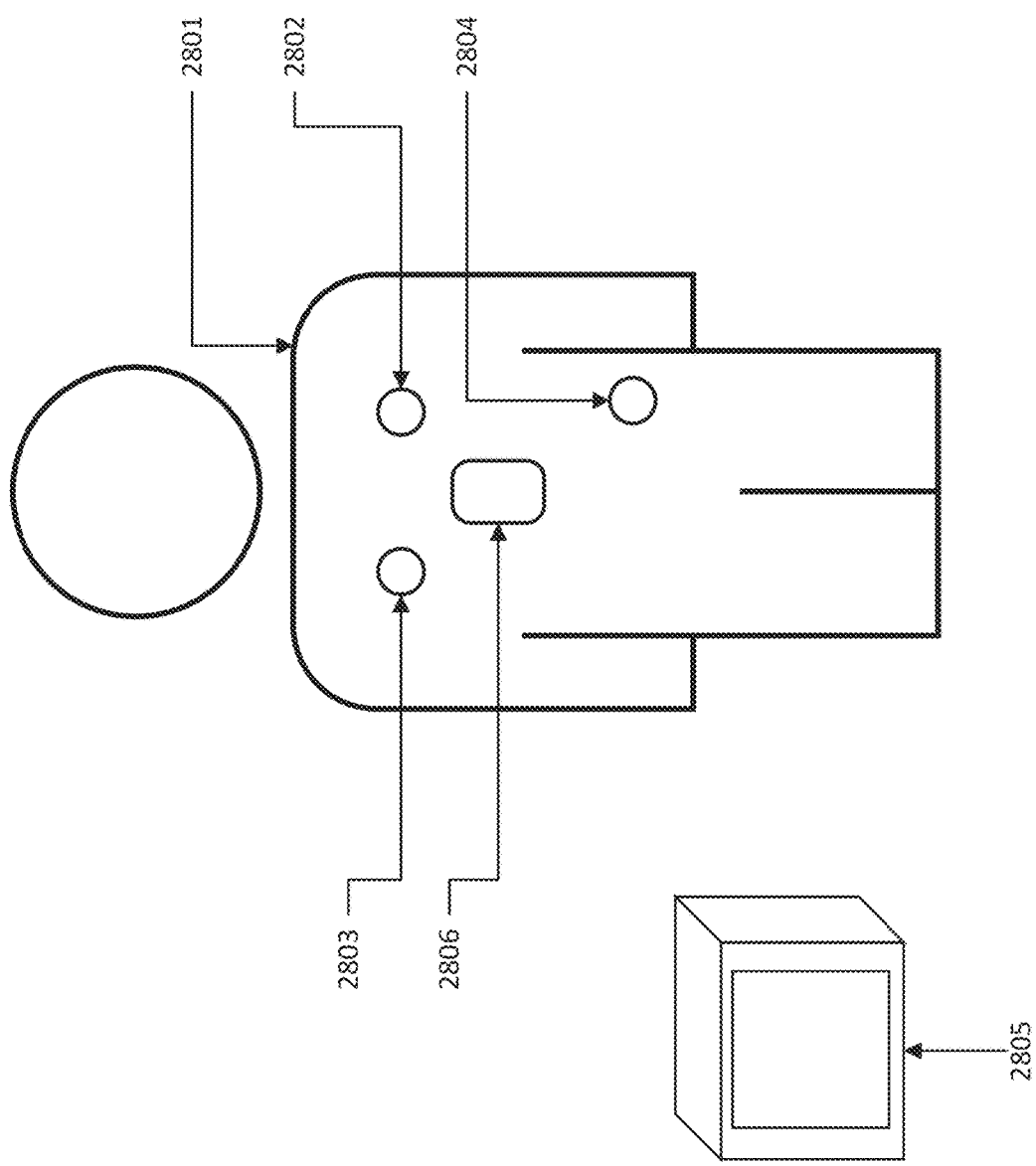
FIG. 28 shows an example embodiment of a wireless heart telemetry monitoring system with an example embodiment of a patient/subject worn telemetry base pack, in accordance with the invention.

FIG. 28 shows another example embodiment of a wireless heart telemetry monitoring system. User 2801 wears heart monitor pads 2802-2804, which wired or wirelessly sends data to wearable patient monitoring base point 2806. The example locations of monitoring pads 2802-2804 are meant for demonstration purposes and are not to be considered the only locations or quantity of pads required for heart telemetry monitoring. In the example shown, 2802-2804 utilize disposable snap on or clip on pads, which are in contact with the patient skin, similar to those used in current heart telemetry systems. Snapped or clipped onto these pads are the reusable devices, which include the hardware required to wired or wirelessly transmit the heart telemetry data to the wearable base point 2806. In wireless embodiments, this hardware, for example, includes, but is not limited to, filtering, MCU, wireless SoC, battery, and isolation technology. The wireless signals from 2802-2804 must be synchronized, in order for the system to work properly using, for example, time of flight calculations and/or synchronized time stamping. One example embodiment of the wireless system, described in FIG. 28, utilizes independent grounds for 2802-2804, while other wireless example embodiments use an interconnected and centralized ground. In example wired embodiments, the signals from pads 2802-2804, including grounds, are connected directly to 2806, and 2806 includes the hardware described above in wireless embodiments. One example embodiment of wireless connectivity between 2802-2804 and 2806 utilizes Bluetooth as its communication method, while other example embodiments use other wireless communication methods, such as, but not limited to, LoRa, NFC, RFID, or other proprietary wireless communication methods. One example embodiment of 2806 utilizes Bluetooth as its wireless communication method to patient monitoring system 2805, while other example embodiments use other wireless communications, such as, but not limited to, Wi-Fi, LoRa, or other proprietary wireless communication methods. In wireless hospital patient monitoring systems, 2805 uses similar communication methods, as described above, for wearable base point 2806. 2805, in the example embodiment shown in FIG. 28, is a wired or wireless bedside patient monitoring system. Other example embodiments use bedside systems connected to hospital wide patient monitoring systems, pocket patient monitoring systems connected to bedside and/or hospital wide patient monitoring systems, independent pocket patient monitoring systems, smart device patient monitoring systems, portable patient monitoring systems, or hospital wide patient monitoring systems, instead of bedside patient monitoring system 2805. 2805 utilizes wired or wireless methods of communication for all example embodiments listed above. Other example embodiments of 2805 use wired TCP/IP or other types of ethernet connections to connect to hospital patient monitoring systems, as described above. 2806, in the example embodiment shown, does not include a screen, in order to save battery life, while some other example embodiments include a screen for convenience. The example placement of 2806 is meant for demonstration purposes and is not to be considered the only location that is used. For example, patients that have pace makers or other implanted devices near or around the area shown, may not be able to have a wireless device in close proximity to their implant, due to interference concerns. In situations in which there is a concern for interference with an implant, 2802-2804 can be connected, via wired methods to 2806, and 2806 can be placed in a non-interfering location on the body. 2806, in the example embodiment shown in FIG. 28, is attached to user 2801, via medical grade adhesives, such as, but not limited to, temporary skin glue, tapes, and/or tegaderm. In other example embodiments, 2806 is a pocket worn or belt clip worn device. The portion of the system worn on the user 2801 in FIG. 28 is designed to be completely waterproof for continuous patient monitoring, including damp locations, such as the bath or shower. Further, other example embodiments are also intrinsically sealed for continuous monitoring in hazardous situations such as, for example, in-patient settings and also in the field on emergency personnel as a real time vitals monitoring system. Other example embodiments use for example, but not limited to, cellular or emergency digital radio interfaces to transmit emergency personnel and military vital information using the heart telemetry system described herein. Further, other example embodiments have reflective melanin bias reducing pulse oximetry systems, as described previously in this document, built into the wearable base point 2806 in example embodiments where the base point is attached directly to the skin.

Total Patient Monitoring System

Figure 29:
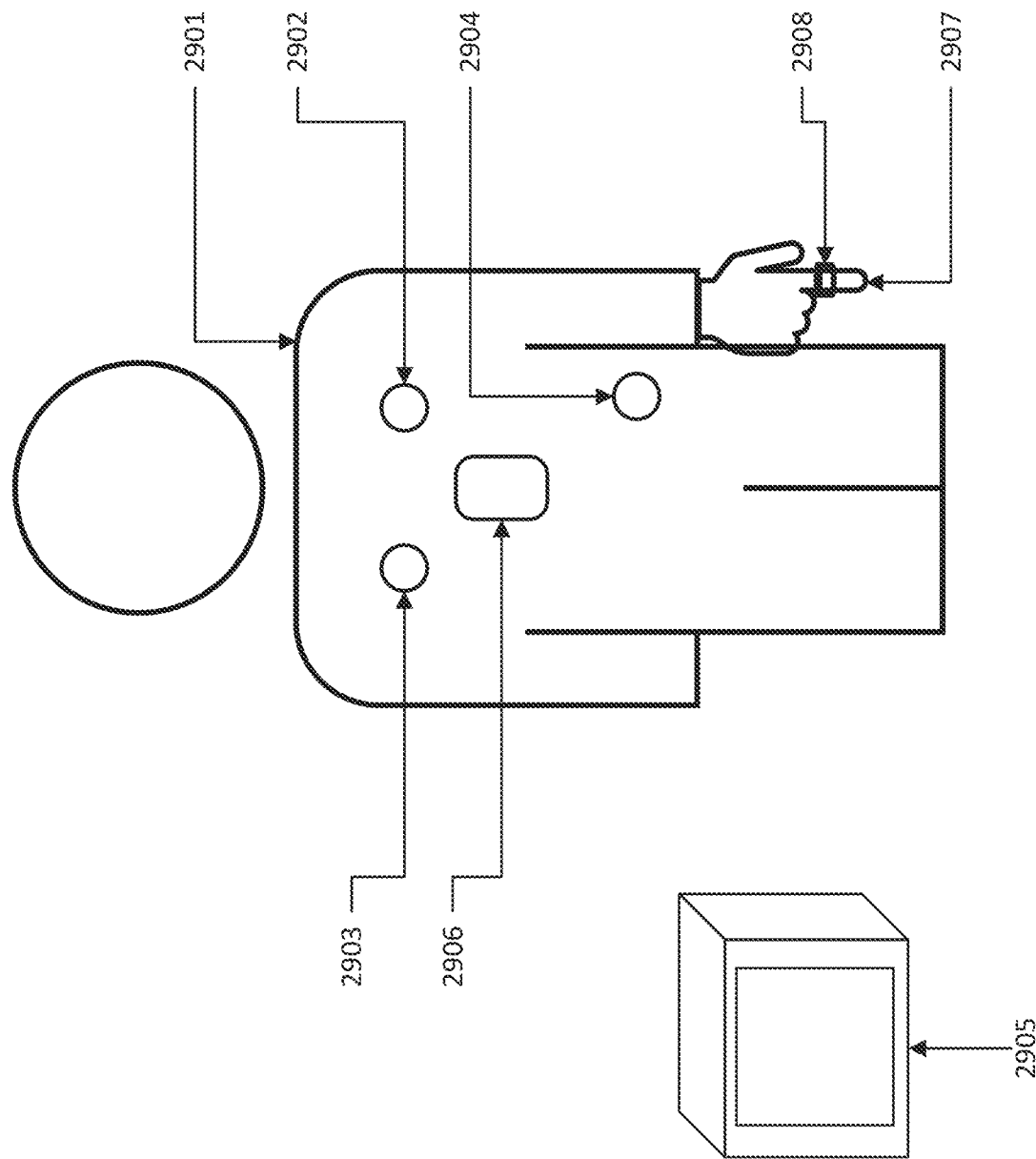
FIG. 29 shows an example embodiment of a wireless total patient monitoring system including, for example, heart telemetry monitoring and pulse oximetry, in accordance with the invention.

FIG. 29 shows an example embodiment of a wireless total patient monitoring system including heart telemetry monitoring and melanin bias reducing pulse oximetry. User 2901 wears heart monitor pads 2902-2904, which wired or wirelessly sends data to wearable patient monitoring base point 2906. The example locations of monitoring pads 2902-2904 are meant for demonstration purposes and are not to be considered the only locations or quantity of pads required for heart telemetry monitoring. In the example shown, 2902-2904 utilize disposable snap on or clip on pads, which are in contact with the patient skin, similar to those used in current heart telemetry systems. Snapped or clipped onto these pads are the reusable devices, which include the hardware required to wired or wirelessly transmit the heart telemetry data to the wearable base point 2906. In wireless embodiments, this hardware includes, but is not limited to, filtering, MCU, wireless SoC, battery, and isolation technology. The wireless signals from 2902-2904 must be synchronized, in order for the system to work properly using, for example, time of flight calculations and/or synchronized time stamping. One example embodiment of the wireless system, described in FIG. 29, utilizes independent grounds for 2902-2904, while other wireless example embodiments use an interconnected and centralized ground. In example wired embodiments, the signals from pads 2902-2904, including grounds, are connected directly to 2906, and 2906 includes the hardware described above in wireless embodiments. One example embodiment of wireless connectivity between 2902-2904 and 2906 utilizes Bluetooth as its communication method, while other example embodiments use other wireless communication methods, such as, but not limited to, LoRa, NFC, RFID, or other proprietary wireless communication methods. One example embodiment of 2906 utilizes Bluetooth as its wireless communication method to patient monitoring system 2905, while other example embodiments use other wireless communications, such as, but not limited to, Wi-Fi, LoRa, or other proprietary wireless communication methods. In wireless hospital patient monitoring systems, 2905 uses similar communication methods, as described above, for wearable base point 2906. 2905, in the example embodiment shown in FIG. 29, is a wired or wireless bedside patient monitoring system. Other example embodiments use bedside systems connected to hospital wide patient monitoring systems, pocket patient monitoring systems connected to bedside and/or hospital wide patient monitoring systems, independent pocket patient monitoring systems, smart device patient monitoring systems, portable patient monitoring systems, or hospital wide patient monitoring systems, instead of bedside patient monitoring system 2905. 2905 utilizes wired or wireless methods of communication for all example embodiments listed above. Other example embodiments of 2805 use wired TCP/IP or other types of ethernet connections to connect to hospital patient monitoring systems, as described above. 2906, in the example embodiment shown, does not include a screen, in order to save battery life, while some example embodiments include a screen for convenience. The example placement of 2906 is meant for demonstration purposes and is not to be considered the only location that is used. For example, patients that have pace makers or other implanted devices near or around the area shown, may not be able to have a wireless device in close proximity to their implant due to interference concerns. In situations where there are concerns for interference with an implant, 2902-2904 can be connected, via wired methods to 2906, and 2906 can be placed in a non-interfering location on the body. 2906, in the example embodiment shown in FIG. 29, is attached to user 2901, via medical grade adhesives, such as, but not limited to, temporary skin glue, tapes, and/or tegaderm. In other example embodiments, 2906 is a pocket worn or belt clip worn device. 2907 represents the example appendage that the melanin bias reducing pulse oximetry portion 2908 is placed on. As described above, 2907 is a finger (shown in FIG. 29), wrist, ankle, arm, leg, or other appendage, as described previously in the finger clip, ring (shown in FIG. 29), and bracelet embodiments, of the pulse oximeter 2908. 2908, as shown as the ring embodiment in FIG. 29 wired or wirelessly communicates with wearable base point 2906 or directly with patient monitoring system 2905, depending on the requirements of the embodiment. In wireless embodiments, 2908 communicates using the wireless communication methods, described in FIG. 29, and elsewhere in this document discussing melanin bias reducing pulse oximetry embodiments to provide a continuous $5^{th}$ vital sign in monitoring applications. The portion of the system worn on the user 2901 in FIG. 29 is designed to be completely waterproof for continuous patient monitoring, including damp locations, such as the bath or shower. Further, other example embodiments are also intrinsically sealed for continuous monitoring in hazardous situations such as, for example, in-patient settings and also in the field on emergency personnel as a real time vitals monitoring system. Other example embodiments use for example, but not limited to, cellular or emergency digital radio interfaces to transmit emergency personnel and military vital information using the heart telemetry and melanin bias reducing system described herein. Further, other example embodiments have reflective melanin bias reducing pulse oximetry systems, as described previously in this document, built into the wearable base point 2906 in example embodiments where the base point is attached directly to the skin.

Other Example Embodiments

Other example embodiments use portions of the embodiments disclosed in this document to create a comfortable and easy to use child monitoring system, which gives parents access to real time location, including geo-fencing, melanin bias reducing pulse oximetry, and heart rate data. Further, other example embodiments use portions of the embodiments disclosed in this document to create a comfortable, fashionable, and easy to use way to incorporate melanin bias reducing pulse oximetry and heart rate monitoring into smart phone systems. Other example embodiments use portions of the embodiments disclosed in this document to create an alert system to replace or augment current fall detection, bed alarm, and call systems used in homes, nursing home facilities, hospitals, and other medical facilities. Other example embodiments are classified as IoT devices and connect to the internet through standalone communications, such as Wi-Fi or cellular communication methods or through smart devices to transmit patient monitoring information to physicians or monitoring services to allow the patient to be monitored globally without in-person visits. Other example embodiments include the melanin bias reducing pulse oximeter technology discussed in this document in smart devices, such as for example smart watches, exercise equipment Fitbits, Holter monitors, smart rings, smart bracelets, and/or other health and fitness devices. Further, other example embodiments include emergency personnel (EMS, police, fire, etc.) and military melanin bias reducing pulse oximetry and heart telemetry monitor systems which interface over cellular or digital emergency service and/or military digital radio communications to provide continuous monitoring including a $5^{th}$ vital sign in the form of blood oxygen saturation levels.

The invention is described in terms of example hardware and software embodiments. The summarized and detailed descriptions of both the hardware and the software are not intended to limit the scope of the invention. The invention is used as a whole or in part for many other types of consumer and industrial devices as well.

While various embodiments of the invention have been described, the description is intended to be exemplary, rather than limiting, and it will be apparent to those of ordinary skill in the art that many more embodiments and implementations are possible that are within the scope of the invention.

Accordingly, the invention is not to be restricted except in light of the attached claims and their equivalents based on the information provided in this patent application. Also, various modifications and changes may be made within the scope of the attached claims.

We claim:

1. A pulse oximeter system for reducing melanin bias and measuring blood oxygen saturation, the system comprising:
   a pulse oximeter comprising:
      a plurality of light sources configured to emit light, wherein a first light source of the plurality of light sources is configured to emit light at a first wavelength and a second light source of the plurality of light sources is configured to emit light at a second wavelength different from the first wavelength;
      a detector configured to:
      detect light emitted by the first light source or the second light source,
      convert light detected from the first light source into a first current signal, and
      convert light detected from the second light source into a second current signal,
      at least one voltage converter configured to convert the first current signal into a first voltage signal or the second current signal into a second voltage signal,
      a communication interface configured to communicate information associated with the first voltage signal or the second voltage signal over a communication network; and
   one or more processors in communication with the at least one voltage converter and the communication interface,
   wherein at least one of the first wavelength and the second wavelength are selected to reduce the melanin bias, and
   wherein blood oxygen saturation measurements are determined by the one or more processors based on the first voltage signal and the second voltage signal received from the at least one voltage converter.

2. The system of claim 1,
   wherein the pulse oximeter further comprises a screen, and
   wherein information associated with the blood oxygen saturation measurements is displayed on the screen.

3. The system of claim 1, further comprising at least one of an inertial measurement unit, accelerometer, gyrometer, altitude sensor, angular velocity sensor, multi-axis inertia sensor, global positioning sensor (GPS), or magnetometer to create motion or location data.

4. The system of claim 3,
   wherein the motion or location data is used to determine at least one of patient tracking data, bed alarm data, or fall detection data,
   wherein the motion or location data or the at least one of patient tracking data, bed alarm data, or fall detection data is transmitted to a patient monitoring system via the communication interface,
   wherein the communication interface is a wired interface or a wireless interface, and
   wherein the patient monitoring system includes at least one of a networked pocket patient monitoring system, an independent pocket patient monitoring system, a portable patient monitoring system, a bedside patient monitoring system, a hospital network patient monitoring system, a Transmission Control Protocol/Internet Protocol (TCP/IP) patient monitoring system, a proprietary communication patient monitoring system, an interconnected hospital wide patient monitoring system, an interconnected pocket/bedside/hospital wide patient monitoring system, a networked bedside patient monitoring system, a portable physician office patient monitoring system, a smart device patient monitoring system, a global patient monitoring system, a cellular patient monitoring system, an emergency service first responder monitoring system, an emergency service first responder radio monitoring system, a military monitoring system, or a military radio monitoring system.

5. The system of claim 1, further comprising:
   a red/green/blue (RGB) display screen for displaying color-coded blood oxygen saturation levels,
   wherein the color-coded blood oxygen saturation levels are identified based on the first voltage signal and the second voltage signal.

6. The system of claim 1,
   wherein the communication interface is a wired interface or wireless interface coupled with a patient monitoring system, and
   wherein the patient monitoring system includes at least one of a networked pocket patient monitoring system, an independent pocket patient monitoring system, a portable patient monitoring system, a bedside patient monitoring system, a hospital network patient monitoring system, a Transmission Control Protocol/Internet Protocol (TCP/IP) patient monitoring system, a proprietary communication patient monitoring system, an interconnected hospital wide patient monitoring system, an interconnected pocket/bedside/hospital wide patient monitoring system, a networked bedside patient monitoring system, a portable physician office patient monitoring system, a smart device patient monitoring system, a global patient monitoring system, a cellular patient monitoring system, an emergency service first responder monitoring system, an emergency service first responder radio monitoring system, a military monitoring system, or a military radio monitoring system.

7. The system of claim 1, wherein additional physiological information is identified determined based on the first voltage signal or the second voltage signal.

8. The system of claim 7, wherein the additional physiological information includes at least one of heart rate information or a plethysmograph.

9. The system of claim 1, wherein the detector is a photodetector.

10. The system of claim 1, wherein the at least one voltage converter is a digital voltage converter or an analog voltage converter.

11. The system of claim 1,
    wherein the pulse oximeter is a ring,
    wherein the plurality of light sources is disposed in a first portion of the ring, and
    wherein the detector is disposed in a second portion opposite the first portion of the ring.

12. The system of claim 11, wherein the ring is waterproof.

13. The system of claim 1, further comprising:
    at least one of a wired standalone screen to display an output, a wireless standalone screen to display the output, a built-in screen to display the output, a built-in screen accompanied by a wired external screen to display the output, a built-in screen accompanied by a wireless external screen to display the output, a built-in screen accompanied by a wired connection to a patient monitoring system to display the output, a built-in screen accompanied by a wireless connection to a patient monitoring system to display the output, wired connection to a patient monitoring system to display the output, a wireless connection to a patient monitoring system to display the output, a smart device display to display the output, a built-in screen accompanied by a smart device display to display the output, a first responder monitor to display the output, a built-in screen accompanied by a first responder monitor to display the output, a military monitor to display the output, or a built-in screen accompanied by a military monitor to display the output, wherein the patient monitoring system includes at least one of a networked pocket patient monitoring system, an independent pocket patient monitoring system, a portable patient monitoring system, a bedside patient monitoring system, a hospital network patient monitoring system, a Transmission Control Protocol/Internet Protocol (TCP/IP) patient monitoring system, a proprietary communication patient monitoring system, an interconnected hospital wide patient monitoring system, an interconnected pocket/bedside/hospital wide patient monitoring system, a networked bedside patient monitoring system, a portable physician office patient monitoring system, a smart device patient monitoring system, a global patient monitoring system, a cellular patient monitoring system, an emergency service first responder monitoring system, an emergency service first responder radio monitoring system, a military monitoring system, or a military radio monitoring system.

14. The system of claim 1, wherein the pulse oximeter article is at least one of a finger clip or a flexible finger clip.

15. The pulse oximeter system of claim 1, wherein the melanin bias is reduced before the one or more processors determine the blood oxygen saturation measurements from the first voltage signal and the second voltage signal received from the at least one voltage converter.

16. A pulse oximeter article for reducing melanin bias and measuring blood oxygen saturation, comprising:
a plurality of light sources comprising:
a first light source configured to emit light at a first wavelength selected for absorption by oxyhemoglobin, and
a second light source configured to emit light at a second wavelength, different from the first wavelength, selected for absorption by deoxyhemoglobin;
a detector configured to:
detect light emitted by the first light source or the second light source,
convert light detected from the first light source into a first current signal, and
convert light detected from the second light source into a second current signal,
at least one voltage converter configured to convert the first current signal into a first voltage signal and the second current signal into a second voltage signal,
a communication interface configured to communicate information associated with the first voltage signal or the second voltage signal over a communication network, and
one or more processors in communication with the at least one voltage converter and the communication interface,
wherein the first wavelength and the second wavelength are selected to reduce the melanin bias, and
wherein blood oxygen saturation measurements are determined by the one or more processors based on the first voltage signal and the second voltage signal received from the at least one voltage converter.

17. The article of claim 16, further comprising at least one of an inertial measurement unit, accelerometer, gyrometer, altitude sensor, angular velocity sensor, multi-axis inertia sensor, global positioning sensor (GPS), or magnetometer to create motion or location data.

18. The article of claim 17,
wherein the motion or location data is used to identify determine at least one of patient tracking data, bed alarm data, or fall detection data,
wherein the motion or location data or the at least one of patient tracking data, bed alarm data, or fall detection data is transmitted to a patient monitoring system via the communication interface,
wherein the communication interface is a wired interface or a wireless interface, and
wherein the patient monitoring system includes at least one of a networked pocket patient monitoring system, an independent pocket patient monitoring system, a portable patient monitoring system, a bedside patient monitoring system, a hospital network patient monitoring system, a Transmission Control Protocol/Internet Protocol (TCP/IP) patient monitoring system, a proprietary communication patient monitoring system, an interconnected hospital wide patient monitoring system, an interconnected pocket/bedside/hospital wide patient monitoring system, a networked bedside patient monitoring system, a portable physician office patient monitoring system, a smart device patient monitoring system, a global patient monitoring system, a cellular patient monitoring system, an emergency service first responder monitoring system, an emergency service first responder radio monitoring system, a military monitoring system, or a military radio monitoring system.

19. The article of claim 16,
wherein the type of pulse oximeter is a flexible ring,
wherein the plurality of light sources is disposed in a first portion of the ring, and
wherein the detector is disposed in a second portion opposite the first portion of the ring.

20. The article of claim 19, wherein the ring is waterproof.

21. The article of claim 16, further comprising,
a red/green/blue (RGB) display screen for displaying color-coded blood oxygen saturation levels,
wherein the color-coded blood oxygen-saturation levels are identified based on the first voltage signal and the second voltage signal.

22. The article of claim 16, further comprising:
at least one of a wired standalone screen to display an output, a wireless standalone screen to display the output, a built-in screen to display the output, a built-in screen accompanied by a wired external screen to display the output, a built-in screen accompanied by a wireless external screen to display the output, a built-in screen accompanied by a wired connection to a patient monitoring system to display the output, a built-in screen accompanied by a wireless connection to a patient monitoring system to display the output, wired connection to a patient monitoring system to display the output, a wireless connection to a patient monitoring system to display the output, a smart device display to display the output, a built-in screen accompanied by a smart device display to display the output, a first responder monitor to display the output, a built-in screen accompanied by a first responder monitor to display the output, a military monitor to display the output, or a built-in screen accompanied by a military monitor to display the output, wherein the patient monitoring system includes at least one of a networked pocket patient monitoring system, an independent pocket patient monitoring system, a portable patient monitoring system, a bedside patient monitoring system, a hospital network patient monitoring system, a Transmission Control Protocol/Internet Protocol (TCP/IP) patient monitoring system, a proprietary communication patient monitoring system, an interconnected hospital wide patient monitoring system, an interconnected pocket/bedside/hospital wide patient monitoring system, a networked bedside patient monitoring system, a portable physician office patient monitoring system, a smart device patient monitoring system, a global patient monitoring system, a cellular patient monitoring system, an emergency service first responder monitoring system, an emergency service first responder radio monitoring system, a military monitoring system, or a military radio monitoring system.

23. The article of claim 16, wherein the detector is a photodetector.

24. The article of claim 16, wherein the at least one voltage converter is a digital voltage converter or an analog voltage converter.

25. The article of claim 16, wherein the pulse oximeter article is at least one of a finger clip or a flexible finger clip.

26. The article of claim 16,
wherein the communication interface is a wired interface or wireless interface coupled with a patient monitoring system, and
wherein the patient monitoring system includes at least one of a networked pocket patient monitoring system, an independent pocket patient monitoring system, a portable patient monitoring system, a bedside patient monitoring system, a hospital network patient monitoring system, a Transmission Control Protocol/Internet Protocol (TCP/IP) patient monitoring system, a proprietary communication patient monitoring system, an interconnected hospital wide patient monitoring system, an interconnected pocket/bedside/hospital wide patient monitoring system, a networked bedside patient monitoring system, a portable physician office patient monitoring system, a smart device patient monitoring system, a global patient monitoring system, a cellular patient monitoring system, an emergency service first responder monitoring system, an emergency service first responder radio monitoring system, a military monitoring system, or a military radio monitoring system.

27. The article of claim 16, wherein additional physiological information is determined based on the first voltage signal or the second voltage signal.

28. The article of claim 27, wherein the additional physiological information includes at least one of heart rate information or a plethysmograph.

29. The pulse oximeter article of claim 16, wherein the melanin bias is reduced before the one or more processors determine the blood oxygen saturation measurements from the first voltage signal and the second voltage signal received from the at least one voltage converter.

* * * * *